US010195423B2

(12) United States Patent
Jiang et al.

(10) Patent No.: US 10,195,423 B2
(45) Date of Patent: Feb. 5, 2019

(54) MULTICHANNEL CLIP DEVICE AND METHODS OF USE

(71) Applicant: Axonics Modulation Technologies, Inc., Irvine, CA (US)

(72) Inventors: Guanqiang Jiang, Irvine, CA (US); John Woock, Costa Mesa, CA (US); Dennis Schroeder, Los Angeles, CA (US); Eric Schmid, Los Angeles, CA (US); Andres Dandler, Newport Beach, CA (US)

(73) Assignee: Axonics Modulation Technologies, Inc., Irvine, CA (US)

( * ) Notice: Subject to any disclaimer, the term of this patent is extended or adjusted under 35 U.S.C. 154(b) by 255 days.

(21) Appl. No.: 15/000,979

(22) Filed: Jan. 19, 2016

(65) Prior Publication Data

US 2017/0203098 A1    Jul. 20, 2017

(51) Int. Cl.
  *A61N 1/08*    (2006.01)
  *A61N 1/36*    (2006.01)
  (Continued)

(52) U.S. Cl.
  CPC ............ *A61N 1/08* (2013.01); *A61N 1/0521* (2013.01); *A61N 1/3605* (2013.01);
  (Continued)

(58) Field of Classification Search
  CPC ............ G01R 31/2887; G01R 31/2891; G01R 31/2893; G01R 31/2808; G01R 1/0425; G01N 15/00; G01N 27/04
  (Continued)

(56) References Cited

U.S. PATENT DOCUMENTS 3,221,731 A * 12/1965 Annis .................. A61B 6/4258
                                                        126/307 A
3,506,949 A    4/1970 Venaleck et al.
(Continued)

FOREIGN PATENT DOCUMENTS

CN    101594906 A    12/2009
EP    1680182 A1    7/2006
(Continued)

OTHER PUBLICATIONS

U.S. Appl. No. 14/827,108, filed Aug. 14, 2015.
(Continued)

*Primary Examiner* — Jermele M Hollington
*Assistant Examiner* — Christopher McAndrew
(74) *Attorney, Agent, or Firm* — Kilpatrick Townsend & Stockton LLP

(57) ABSTRACT

A multichannel clip device and methods of use that facilitate connection of multiple electrical components of a first device and a second device for testing and/or verification are provided herein. Such multichannel clip devices can include a spring-loaded clip having multiple electrical contacts for coupling with a contact portion of a first device and which are connected to a proximal connector through a flexible stimulation cable. The contacts can be included within a neurostimulation lead connector and the proximal connector adapted to couple with standard connectors on a clinician programmer, each contact being coupled to a corresponding contact of the proximal connector to define multiple separate channels. Such clip devices allow clinicians to test and/or verify multiple neurostimulation lead electrodes with a clinician programmers without requiring separate connection of each electrodes to a probe or test device and further allows for repeated sequencing or multi-plexing of neurostimulation leads during testing.

33 Claims, 22 Drawing Sheets

(51) Int. Cl.
*A61N 1/372* (2006.01)
*A61N 1/05* (2006.01)

(52) U.S. Cl.
CPC ..... *A61N 1/36007* (2013.01); *A61N 1/36017* (2013.01); *A61N 1/37241* (2013.01); *A61N 1/37247* (2013.01); *A61N 1/0558* (2013.01); *A61N 2001/083* (2013.01)

(58) Field of Classification Search
USPC ............................................ 324/693, 750.25
See application file for complete search history.

(56) References Cited

U.S. PATENT DOCUMENTS

| | | | |
|---|---|---|---|
| 3,646,940 A | 3/1972 | Timm et al. | |
| 3,899,239 A | 8/1975 | Allard | |
| 4,019,518 A | 4/1977 | Maurer et al. | |
| 4,044,774 A | 8/1977 | Corbin et al. | |
| 4,132,946 A | 1/1979 | Holdren et al. | |
| 4,210,383 A | 7/1980 | Davis | |
| 4,340,062 A | 7/1982 | Thompson et al. | |
| 4,541,100 A * | 9/1985 | Sutton | G06F 11/25 375/224 |
| 4,558,702 A | 12/1985 | Barreras et al. | |
| 4,590,946 A * | 5/1986 | Loeb | A61N 1/0558 600/375 |
| 4,618,208 A | 10/1986 | Igarashi | |
| 4,744,371 A * | 5/1988 | Harris | A61N 1/375 439/668 |
| 4,749,362 A | 6/1988 | Hoffman et al. | |
| 4,981,441 A | 1/1991 | Ignasiak | |
| 5,366,493 A | 11/1994 | Scheiner et al. | |
| 5,482,038 A * | 1/1996 | Ruff | A61B 5/0492 439/482 |
| 5,557,210 A * | 9/1996 | Cappa | A61N 1/05 324/538 |
| 5,571,998 A | 11/1996 | Momoi | |
| 5,679,022 A | 10/1997 | Cappa et al. | |
| 5,690,693 A | 11/1997 | Wang et al. | |
| 5,692,926 A | 12/1997 | Jarl | |
| 5,702,428 A | 12/1997 | Tippey et al. | |
| 5,702,431 A | 12/1997 | Wang et al. | |
| 5,735,887 A | 4/1998 | Barreras, Sr. et al. | |
| 5,741,316 A | 4/1998 | Chen et al. | |
| 5,788,524 A | 8/1998 | Balyasny et al. | |
| 5,876,423 A | 3/1999 | Braun | |
| 6,027,456 A | 2/2000 | Feler et al. | |
| 6,035,237 A | 3/2000 | Schulman et al. | |
| 6,052,624 A | 4/2000 | Mann | |
| 6,055,456 A | 4/2000 | Gerber | |
| 6,057,513 A | 5/2000 | Ushikoshi et al. | |
| 6,067,474 A | 5/2000 | Schulman et al. | |
| 6,076,017 A | 6/2000 | Taylor et al. | |
| 6,172,556 B1 | 1/2001 | Prentice | |
| 6,178,353 B1 | 1/2001 | Griffith et al. | |
| 6,191,365 B1 | 2/2001 | Avellanet | |
| 6,194,905 B1 | 2/2001 | Pivnichny et al. | |
| 6,205,361 B1 * | 3/2001 | Kuzma | A61N 1/05 607/116 |
| 6,208,894 B1 | 3/2001 | Schulman et al. | |
| 6,212,431 B1 | 4/2001 | Hahn et al. | |
| 6,221,513 B1 | 4/2001 | Lasater | |
| 6,246,911 B1 | 6/2001 | Seligman | |
| 6,249,703 B1 | 6/2001 | Stanton et al. | |
| 6,265,789 B1 | 7/2001 | Honda et al. | |
| 6,306,100 B1 | 10/2001 | Prass | |
| 6,315,721 B2 | 11/2001 | Schulman et al. | |
| 6,354,991 B1 | 3/2002 | Gross et al. | |
| 6,360,750 B1 | 3/2002 | Gerber et al. | |
| 6,393,325 B1 | 5/2002 | Mann et al. | |
| 6,438,423 B1 | 8/2002 | Rezai et al. | |
| 6,442,434 B1 | 8/2002 | Zarinetchi et al. | |
| 6,466,817 B1 | 10/2002 | Kaula et al. | |
| 6,505,075 B1 | 1/2003 | Weiner | |
| 6,516,227 B1 | 2/2003 | Meadows et al. | |
| 6,584,355 B2 | 6/2003 | Stessman | |
| 6,600,954 B2 | 7/2003 | Cohen et al. | |
| 6,609,031 B1 | 8/2003 | Law et al. | |
| 6,609,032 B1 | 8/2003 | Woods et al. | |
| 6,652,449 B1 | 11/2003 | Gross et al. | |
| 6,662,035 B2 * | 12/2003 | Sochor | A61N 1/0529 439/909 |
| 6,662,051 B1 | 12/2003 | Eraker et al. | |
| 6,721,603 B2 | 4/2004 | Zabara et al. | |
| 6,735,474 B1 | 5/2004 | Loeb et al. | |
| 6,745,077 B1 | 6/2004 | Griffith et al. | |
| 6,809,701 B2 | 10/2004 | Amundson et al. | |
| 6,836,684 B1 | 12/2004 | Rijkhoff et al. | |
| 6,847,849 B2 | 1/2005 | Mamo et al. | |
| 6,892,098 B2 | 5/2005 | Ayal et al. | |
| 6,895,280 B2 | 5/2005 | Meadows et al. | |
| 6,896,651 B2 | 5/2005 | Gross et al. | |
| 6,901,287 B2 | 5/2005 | Davis et al. | |
| 6,941,171 B2 | 9/2005 | Mann et al. | |
| 6,971,393 B1 | 12/2005 | Mamo et al. | |
| 6,989,200 B2 | 1/2006 | Byers et al. | |
| 6,990,376 B2 | 1/2006 | Tanagho et al. | |
| 6,999,819 B2 | 2/2006 | Swoyer et al. | |
| 7,051,419 B2 | 5/2006 | Schrom et al. | |
| 7,054,689 B1 | 5/2006 | Whitehurst et al. | |
| 7,069,081 B2 | 6/2006 | Biggs et al. | |
| 7,127,298 B1 | 10/2006 | He et al. | |
| 7,142,925 B1 | 11/2006 | Bhadra et al. | |
| 7,146,219 B2 | 12/2006 | Sieracki et al. | |
| 7,151,914 B2 | 12/2006 | Brewer | |
| 7,167,749 B2 | 1/2007 | Biggs et al. | |
| 7,177,690 B2 | 2/2007 | Woods et al. | |
| 7,177,698 B2 | 2/2007 | Klosterman et al. | |
| 7,181,286 B2 | 2/2007 | Sieracki et al. | |
| 7,187,978 B2 | 3/2007 | Malek et al. | |
| 7,191,005 B2 | 3/2007 | Stessman | |
| 7,212,110 B1 | 5/2007 | Martin et al. | |
| 7,225,032 B2 | 5/2007 | Schmeling et al. | |
| 7,231,254 B2 | 6/2007 | DiLorenzo | |
| 7,234,853 B2 | 6/2007 | Givoletti | |
| 7,245,972 B2 | 7/2007 | Davis | |
| 7,286,880 B2 | 10/2007 | Olson et al. | |
| 7,305,268 B2 | 12/2007 | Gliner et al. | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,328,068 B2 | 2/2008 | Spinelli et al. | |
| 7,330,764 B2 | 2/2008 | Swoyer et al. | |
| 7,359,751 B1 | 4/2008 | Erickson et al. | |
| 7,369,894 B2 | 5/2008 | Gerber | |
| 7,386,348 B2 | 6/2008 | North et al. | |
| 7,387,603 B2 | 6/2008 | Gross et al. | |
| 7,396,265 B2 | 7/2008 | Darley et al. | |
| 7,415,308 B2 | 8/2008 | Gerber et al. | |
| 7,444,181 B2 | 10/2008 | Shi et al. | |
| 7,450,991 B2 | 11/2008 | Smith et al. | |
| 7,460,911 B2 | 12/2008 | Cosendai et al. | |
| 7,463,928 B2 | 12/2008 | Lee et al. | |
| 7,470,236 B1 | 12/2008 | Kelleher et al. | |
| 7,483,752 B2 | 1/2009 | Von Arx et al. | |
| 7,496,404 B2 | 2/2009 | Meadows et al. | |
| 7,515,967 B2 | 4/2009 | Phillips et al. | |
| 7,521,634 B2 * | 4/2009 | Clem | G01R 1/06788 174/113 R |
| 7,532,936 B2 | 5/2009 | Erickson et al. | |
| 7,539,538 B2 | 5/2009 | Parramon et al. | |
| 7,551,960 B2 | 6/2009 | Forsberg et al. | |
| 7,555,346 B1 | 6/2009 | Woods et al. | |
| 7,565,203 B2 | 7/2009 | Greenberg et al. | |
| 7,578,819 B2 | 8/2009 | Bleich et al. | |
| 7,580,752 B2 | 8/2009 | Gerber et al. | |
| 7,582,053 B2 | 9/2009 | Gross et al. | |
| 7,608,072 B2 * | 10/2009 | Swanson | A61N 1/05 606/41 |
| 7,617,002 B2 | 11/2009 | Goetz | |
| 7,636,602 B2 * | 12/2009 | Baru Fassio | A61B 5/112 607/48 |
| 7,640,059 B2 | 12/2009 | Forsberg et al. | |

(56) References Cited

U.S. PATENT DOCUMENTS

| | | |
|---|---|---|
| 7,643,880 B2 | 1/2010 | Tanagho et al. |
| 7,676,275 B1 | 3/2010 | Farazi et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,954,148 B2 | 2/2015 | Labbe et al. |
| 8,989,861 B2 | 3/2015 | Su et al. |
| 9,089,712 B2 | 7/2015 | Joshi et al. |
| 9,108,063 B2 | 8/2015 | Olson et al. |
| 2003/0028231 A1 | 2/2003 | Partridge et al. |
| 2004/0172115 A1 | 9/2004 | Miazga et al. |
| 2004/0230282 A1 | 11/2004 | Cates et al. |
| 2005/0010265 A1* | 1/2005 | Baru Fassio ........... A61B 5/112 607/48 |
| 2005/0104577 A1 | 5/2005 | Matei et al. |
| 2005/0119545 A1* | 6/2005 | Swanson ............. A61B 18/1492 600/374 |
| 2005/0119648 A1* | 6/2005 | Swanson ................. A61N 1/05 606/41 |
| 2006/0041295 A1 | 2/2006 | Osypka |
| 2006/0142822 A1 | 6/2006 | Tulgar |
| 2006/0206166 A1 | 9/2006 | Weiner |
| 2007/0255369 A1 | 11/2007 | Bonde et al. |
| 2007/0265675 A1 | 11/2007 | Lund et al. |
| 2007/0267213 A1* | 11/2007 | Clem ................. G01R 1/06788 174/78 |
| 2007/0293914 A1 | 12/2007 | Woods et al. |
| 2008/0161874 A1 | 7/2008 | Bennett et al. |
| 2008/0183236 A1 | 7/2008 | Gerber |
| 2009/0012592 A1 | 1/2009 | Buysman et al. |
| 2010/0076254 A1 | 3/2010 | Jimenez et al. |
| 2010/0076534 A1 | 3/2010 | Mock |
| 2010/0160997 A1 | 6/2010 | Johnson et al. |
| 2010/0190375 A1 | 7/2010 | Rohde |
| 2010/0256696 A1 | 10/2010 | Schleicher et al. |
| 2011/0208265 A1 | 8/2011 | Erickson et al. |
| 2011/0251662 A1 | 10/2011 | Griswold et al. |
| 2011/0257503 A1 | 10/2011 | Mehdizadeh et al. |
| 2011/0270269 A1 | 11/2011 | Swoyer et al. |
| 2011/0282416 A1 | 11/2011 | Hamann et al. |
| 2011/0301667 A1 | 12/2011 | Olson et al. |
| 2011/0306974 A1* | 12/2011 | Swanson ............. A61B 18/1492 606/52 |
| 2011/0313427 A1 | 12/2011 | Gindele et al. |
| 2012/0041512 A1 | 2/2012 | Weiner |
| 2012/0046712 A1 | 2/2012 | Woods et al. |
| 2012/0053665 A1 | 3/2012 | Stolz et al. |
| 2012/0089002 A1* | 4/2012 | Mackie ............. H01R 13/2471 600/394 |
| 2012/0095478 A1 | 4/2012 | Wang et al. |
| 2012/0130397 A1 | 5/2012 | Reddy et al. |
| 2012/0130448 A1 | 5/2012 | Woods et al. |
| 2012/0153967 A1 | 6/2012 | Koop |
| 2012/0191169 A1 | 7/2012 | Rothstein et al. |
| 2012/0203320 A1 | 8/2012 | DiGiore et al. |
| 2012/0276854 A1 | 11/2012 | Joshi et al. |
| 2012/0276856 A1 | 11/2012 | Joshi et al. |
| 2012/0310317 A1 | 12/2012 | Lund et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0018447 A1 | 1/2013 | Ollivier et al. |
| 2013/0131766 A1 | 5/2013 | Crosby et al. |

(56) References Cited

U.S. PATENT DOCUMENTS

| | | | |
|---|---|---|---|
| 2013/0150925 A1 | 6/2013 | Vamos et al. | |
| 2013/0150936 A1 | 6/2013 | Takahashi | |
| 2013/0150939 A1 | 6/2013 | Burnes et al. | |
| 2013/0184773 A1 | 7/2013 | Libbus et al. | |
| 2013/0197608 A1 | 8/2013 | Eiger | |
| 2013/0207863 A1 | 8/2013 | Joshi | |
| 2013/0274625 A1* | 10/2013 | Sarma | A61B 5/048 600/544 |
| 2013/0310894 A1 | 11/2013 | Trier | |
| 2013/0331909 A1 | 12/2013 | Gerber | |
| 2014/0222112 A1 | 8/2014 | Fell | |
| 2014/0237806 A1 | 8/2014 | Smith et al. | |
| 2014/0277270 A1 | 9/2014 | Parramon et al. | |
| 2015/0214604 A1 | 7/2015 | Zhao et al. | |

FOREIGN PATENT DOCUMENTS

| | | |
|---|---|---|
| EP | 1680182 B1 | 7/2006 |
| EP | 2243509 A1 | 10/2010 |
| JP | 2009254901 A * | 11/2009 |
| JP | 2009254902 A * | 11/2009 |
| WO | WO 1998/20933 A1 | 5/1998 |
| WO | WO 00/56677 A1 | 3/2000 |
| WO | WO 00/27469 A2 | 5/2000 |
| WO | WO 2003/084433 A3 | 10/2003 |
| WO | WO 2006/116205 A1 | 11/2006 |
| WO | WO 2007/022180 A1 | 2/2007 |
| WO | WO 2008/021524 A2 | 2/2008 |
| WO | WO 2008/153726 A2 | 12/2008 |
| WO | WO 2009/102536 A1 | 8/2009 |
| WO | WO 2009/135075 A1 | 11/2009 |
| WO | WO 2010/107751 A2 | 9/2010 |
| WO | WO 2011/059565 A1 | 5/2011 |
| WO | WO 2013/063798 A1 | 5/2013 |
| WO | WO 2013/070490 A1 | 5/2013 |
| WO | WO 2013/156038 A1 | 10/2013 |

OTHER PUBLICATIONS

U.S. Appl. No. 14/991,752, filed Jan. 8, 2016.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.
Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.
Tanagho, E., et al., Bladder Pacemaker: Scientific Basis and Clinical Future, Urology, Dec. 1982, vol. 20, No. 6, pp. 614-619.

* cited by examiner

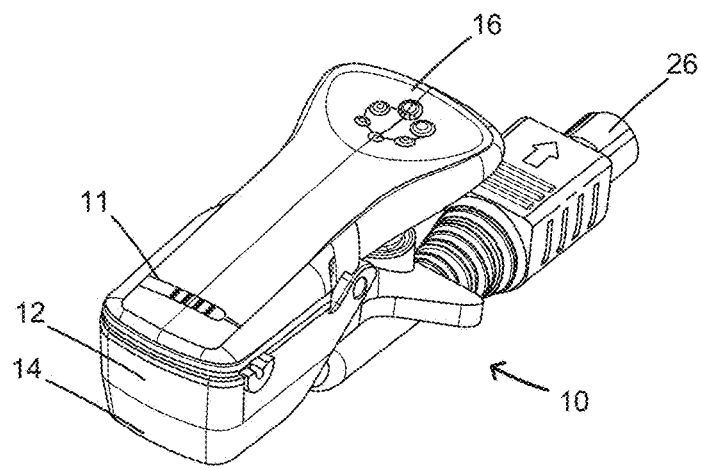
FIG. 5A
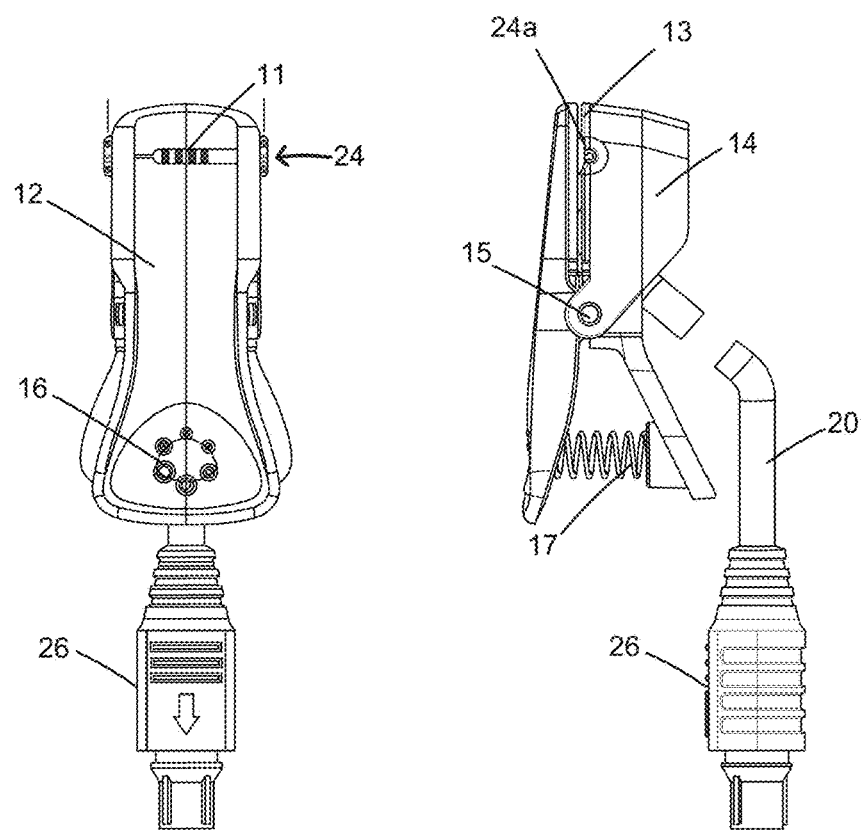
FIG. 5B  FIG. 5C

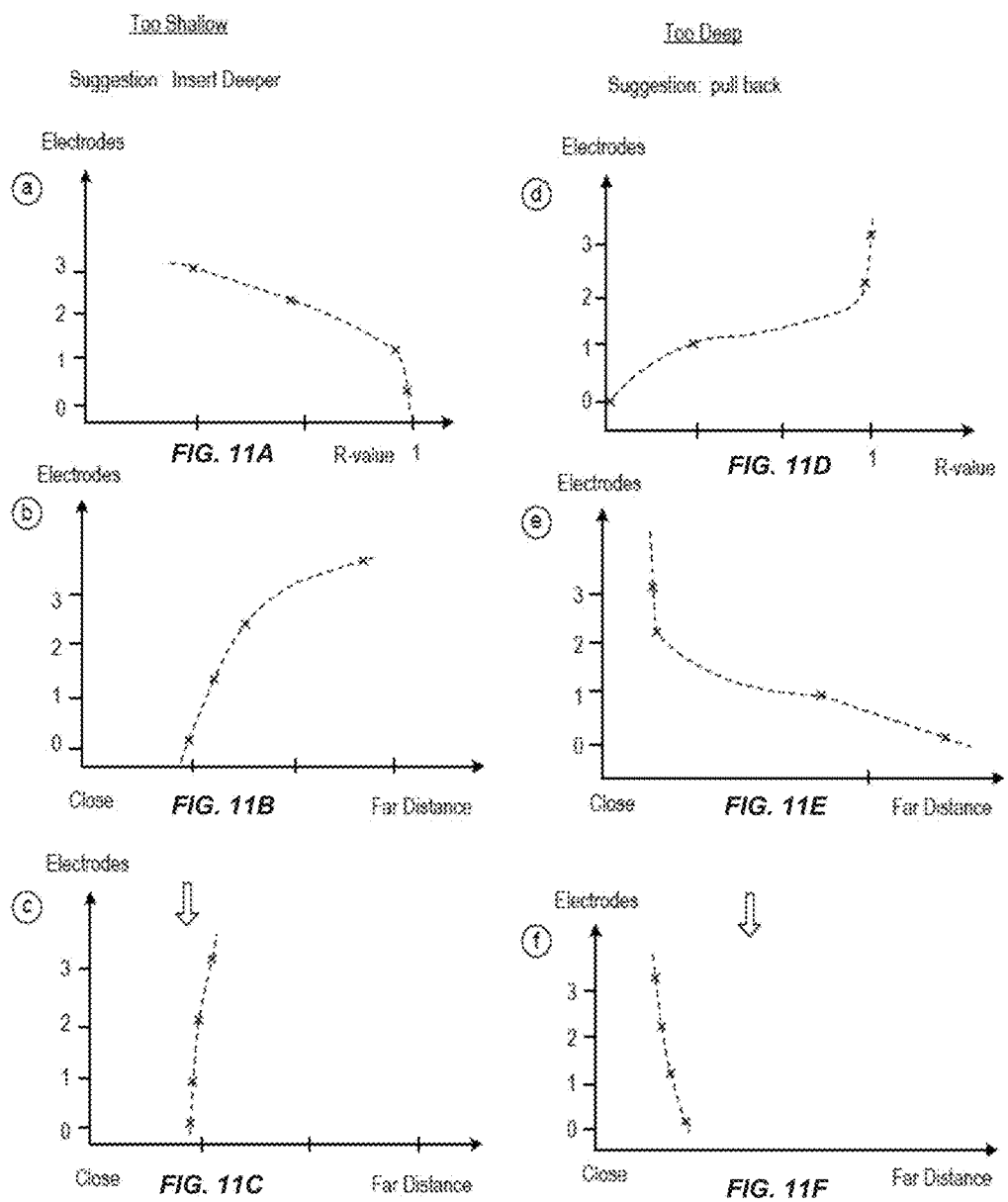

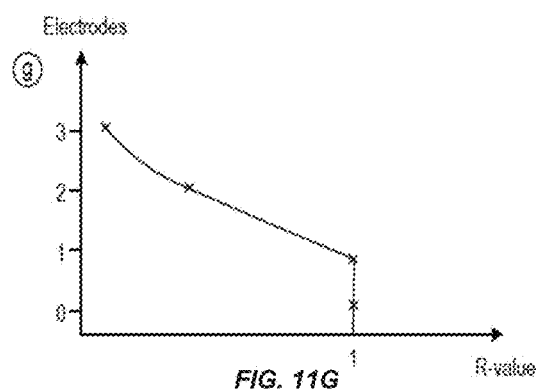
FIG. 11G
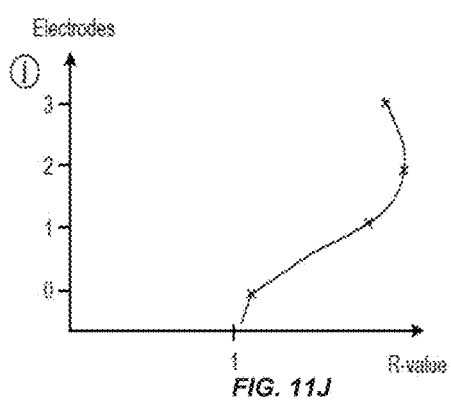
FIG. 11J
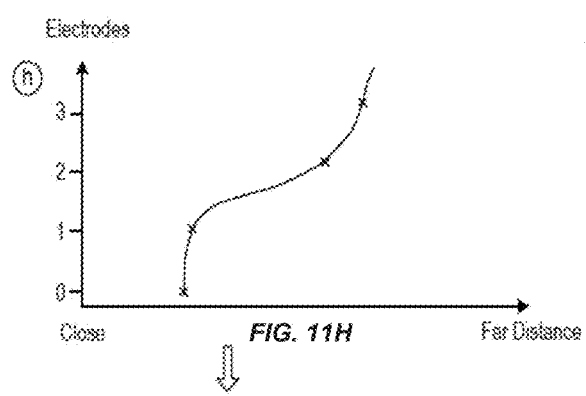
FIG. 11H
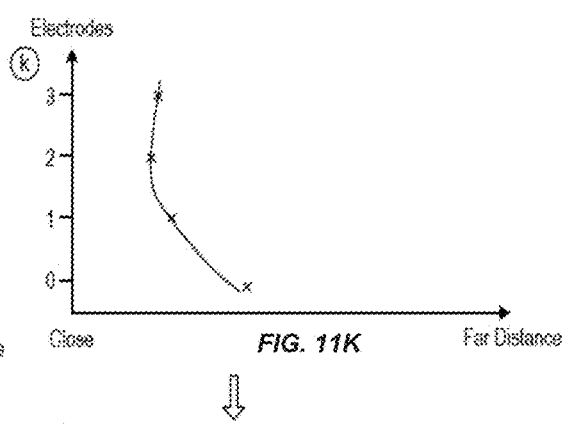
FIG. 11K
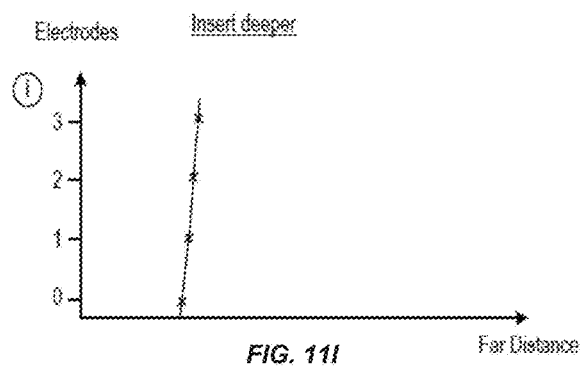
FIG. 11I
FIG. 11L

MULTICHANNEL CLIP DEVICE AND METHODS OF USE

CROSS-REFERENCES TO RELATED APPLICATIONS

The present application is related to U.S. Non-Provisional patent application Ser. Nos. 14/827,108, entitled "Electromyographic Lead Positioning and Stimulation Titration in a Nerve Stimulation System for Treatment of Overactive Bladder"; Ser. No. 14/827,095, entitled "Integrated Electromyographic Clinician Programmer For Use With an Implantable Neurostimulator"; and Ser. No. 14/827,067, entitled "Systems and Methods for Neurostimulation Electrode Configurations Based on Neural Localization;" each of which was filed Aug. 14, 2015 and is assigned to the same assignee and incorporated herein by reference in its entirety for all purposes.

FIELD OF THE INVENTION

The present invention relates to neurostimulation treatment systems and associated devices, as well as methods of testing, implantation and configuration of such treatment systems.

BACKGROUND OF THE INVENTION

Treatments with implantable neurostimulation systems have become increasingly common in recent years. While such systems have shown promise in treating a number of conditions, effectiveness of treatment may vary considerably between patients. A number of factors may lead to the very different outcomes that patients experience, and viability of treatment can be difficult to determine before implantation. In many such applications, a stimulation lead includes an array of electrodes to treat one or more target nerve structures. The electrodes are often mounted together on a multi-electrode lead, and the lead implanted in tissue of the patient at a position that is intended to result in electrical coupling of the electrode to the target nerve structure, typically with at least a portion of the coupling being provided via intermediate tissues.

Stimulation leads may be placed transcutaneously as part of the lead placement procedure during which the stimulation lead may be tested for electrical continuity and to verify accurate placement through impedance, EMG, patient response to stimulation, and the like, before it is implanted permanently.

Neurostimulation leads often include a plurality of electrodes that are individually verified. The conventional approach in sacral neuromodulation therapy is to use a single-contact, such as a "j-clip" or alligator clip, similar to those often used in electronics applications. The single-contact clip is connected to one electrode to test one electrode channel at a time. For stimulation leads having multiple electrodes, this one-at-a-time process must be repeated until each channel has been verified. Repetitively performing verification adds needless time and complexity to the medical procedure, consequently increasing procedure cost and length of patient exposure to the procedure. Therefore, a need exists to provide apparatus and methods that allow for verifying stimulation leads with a plurality of electrodes without the repetitive approach currently used.

BRIEF SUMMARY OF THE INVENTION

The present invention generally relates to devices for testing and/or verification of multiple electrical components and associated methods of use. In particular, the invention relates to a multichannel clip device that facilitate rapid testing and/or verification of multiple neurostimulation electrodes of a neurostimulation lead with a programming device, the neurostimulation lead being coupled with the programming device via the multichannel clip device.

In one aspect, the invention provides a multichannel clip for testing of a plurality of electrical components of a first device. The clip can include a pair of opposing members that are pivotally coupled so as to be movable between an open position and closed position. In the open position, the opposing members are spaced apart to receive a contact portion of the first device therebetween, the contact portion having contacts electrically coupled with the plurality of electrical components. In the closed position, the opposing members are positioned adjacent each other to secure the contact portion of the first device therebetween. A plurality of electrical contacts, such as a plurality of connector pins, are positioned on an inside surface between the opposing members to electrically couple with the plurality of electrical contacts on the contact portion of the first device secured between the opposing members in the closed position. The clip can further include a stimulation cable having a plurality of conductors coupling the plurality of electrical contacts of the clip to a proximal cable connector. The proximal cable connector includes a plurality of connector contacts and configured for electrically coupling with a second device, such as a testing or programming device. The plurality of conductors correspond to the plurality of electrical contacts of the clip such that each of conductors provides a separate channel between a respective electrical component of the plurality and the second device to allow testing of each of the plurality of electrical components of the first device with the second device via the clip. In one aspect, the stimulation cable and associated proximal cable connector are permanently and fixedly attached to the test-clip such that each component can be tested without requiring separate attachment to the test device. In some embodiments, the proximal connector can be configured according to a connector standard or type to facilitate connection with a standard connector of a testing or programming device.

In various embodiments, the multichannel clip includes a pair of opposing members that define a pair of jaws that are biased toward the closed position by an urging member, such as one or more springs. Each of the pair of opposing members can further include a handle along a proximal portion thereof. At least one handle of the pair of opposing members can include a gripping surface to facilitate manual actuation of the clip with a single hand of a user.

In various embodiments, the clip can include a connector holder disposed between the pair of opposing members. The connector holder can include top and bottom portions that are pivotally coupled such that the top and bottom portions engage the contact portion of the first device when the opposing jaws are in the closed position. The connector holder can be molded to correspond to a shape of the contact portion of the first device being secured within the clip. The connector holder can be molded asymmetrically to only receive the contact portion of the first device in a predetermined orientation. The plurality of electrical contacts of the clip can be positioned in an arrangement that corresponds to that of the electrical contacts on the contact portion of the first device. The electrical contacts can be defined by a plurality of pins that extend through a plurality of holes in the connector holder to engage the plurality of electrical contacts on the contact portion of the first device when secured between the pair of opposing members in the closed position. The clip can further include a graphical representation viewable by a user that indicates a desired position and/or orientation of the portion of the contact portion of the first device within the clip to assist a user in placement of the contact portion of the first device within the clip.

In another aspect, the multichannel clip includes a pair of jaws pivotally coupled and movable between an open position in which a distal portion of each of the jaws are spaced apart and a closed position in which the jaws secure a contact portion of the first device therebetween. The contact portion of the first device includes a plurality of electrical contacts corresponding to a plurality of electrical components of the first device. A plurality of electrical contacts are positioned within the clip so as to electrically couple with the plurality of electrical contacts on the contact portion of the first device when secured between the pair of jaws in the closed position. The clip further includes a manually operable actuator for facilitating movement of the pair of jaws between the closed position and the open position to facilitate removal of the contact portion of the first device from the closed position. The clip can also include a stimulation cable having a plurality of conductors electrically coupling the plurality of electrical contacts to a proximal cable connector. The proximal cable connector includes a plurality of connector contacts and is configured for connection with a programming device. The plurality of conductors correspond to the plurality of electrical contacts of the clip such that each of conductors provides a separate channel between the plurality of electrodes of the first device and the programming device. In various embodiments, the plurality of electrical contacts of the clip are concurrently electrically coupled with the plurality of electrical contacts of the first device portion when secured in the closed position and the stimulation cable. In various embodiments, the proximal cable end connector is permanently and fixedly attached to the test-clip such that a user can stimulate the plurality of electrodes concurrently, in a rapid sequence, or in varying combinations with the programming device without adjusting any electrical connections of the clip between stimulations.

In another aspect, the multichannel clip includes a clip having a first portion and a second portion movable relative each other between an open position in which the top and bottom portions are spaced apart and a closed position in which the top and bottom portions are urged towards each other. The open position is adapted for receiving a contact portion of a first device, the portion having a plurality of electrical contacts corresponding to a plurality of electrical components of the first device. The closed position is adapted for securing the contact portion of the first device between the first and second portions. The clip includes a plurality of electrical contacts positioned to electrically couple with the plurality of electrical contacts on the contact portion of the first device when secured in the closed position. The clip further includes a stimulation cable having a plurality of conductors extending therethrough electrically coupling the plurality of electrical contacts to a proximal cable connector. The proximal cable connector includes a plurality of connector contacts and is configured for electrically coupling with a second device to allow verification and/or testing of each of the plurality of electrical components of the first device with the second device when coupled to the connector. The manually operable actuation mechanism is adapted to effect movement of the first and second portions of the clip relative each other when in the closed position to facilitate release of the contact portion of the first device from the clip.

In yet another aspect, the invention provides methods of verifying and/or testing a plurality of electrical components of a first device. In such methods, a user may secure a contact portion of a first device between opposing members of the clip in the closed position so that a plurality of connector contacts disposed along an inside surface between the opposing members electrically couple with a plurality of electrical contacts of the first device that correspond to the plurality of electrical components. A proximal cable connector of the clip can be connected to a corresponding connector of a second device. The proximal cable connector can be a multichannel connector having a plurality of connector contacts that correspond to and are electrically coupled with the plurality of connector contacts disposed between the opposing members via a plurality of electrical conductors such that the clip provides a separate channel between each of the plurality of electrical components of the first device and the second device. The clinician can then test and/or verify each of the plurality of electrical components of the first device with the second device via the multichannel clip closed on the contact portion of the first device remains secured between opposing members and connected to the second device. In various embodiments, the second device comprises a programming device and the first device comprises a neurostimulation device. Verifying and/or testing each of the plurality of electrical components can include communicating, stimulating and/or measuring through the separate channels provided by the multichannel clip, which can occur concurrently, in a particular sequence or in varying combinations, as desired. In one aspect, multiplexing can utilize a pre-determined programmable instruction stored on a readable memory accessed by the second device.

In another aspect, the invention provides a multichannel test clip for testing of a neurostimulation lead. Such a test clip can include a pair of opposing members pivotally coupled together, each member having a jaw along a distal portion thereof and a handle along a proximal portion thereof. The pair of members are movable by manual articulation of the handles between an open position in which opposing jaws are spaced apart to receive a proximal portion of the neurostimulation lead and a closed position in which opposing jaws are adjacent one another. The pair of opposing members are biased by an urging member towards the closed position so as to secure the proximal end of the lead between opposing jaws when in the closed position. The urging member can be a spring extending between opposing members. The clip further includes a lead connector that is disposed along an inside of opposing jaws of the pair of opposing members and that includes a plurality of electrical contacts, such as a plurality of contact pins, arranged to electrically couple with a plurality of electrical contacts on the proximal end of the lead when secured between the opposing jaws in the closed position. The plurality of electrical contacts of the lead correspond to a plurality of neurostimulation electrodes on a distal portion of the lead. The clip further includes a proximal cable connector having a plurality of connector contacts that correspond to the plurality of electrical contacts of the lead connector. The proximal cable connector is configured for electrically coupling with a corresponding connector of a programming device. The clip further includes a stimulation cable having a plurality of conductors extending therethrough that electrically couples corresponding electrical contacts of the lead connector and the proximal connector to provide a separate channel between a respective neurostimulation electrode of the lead and the programming device to allow testing of each of the plurality of neurostimulation electrodes with the programming device. In various embodiments, the stimulation cable and associated proximal cable connector are permanently and fixedly attached to the test-clip. In various embodiments the proximal connector is configured according to a connector standard or type of connector, such as an ODU Mini-Snap cylindrical connector plug.

In various embodiments, the multichannel clip includes a pair of opposing members, each member having a jaw along a distal portion thereof and a handle along a proximal portion thereof. At least one of the handles of the pair of opposing members can include a gripping surface to facilitate manual actuation of the pair of opposing member by manually pressing of the gripping surface with a single hand of a user. The gripping surface can be defined as a thumb depression and can include a plurality of tactile gripping features to facilitate manual articulation of the clip.

In various embodiments, the multichannel clip includes a connector holder disposed between opposing members that define the opposing jaws that receive a proximal contact portion of the neurostimulation lead. The connector holder can include top and bottom portions that are pivotally coupled so that the top and bottom portions engage the proximal end of the lead when in the closed position. One or both of the top and bottom members can include a groove for receiving the proximal portion of the neurostimulation lead, the proximal portion of the neurostimulation lead being substantially cylindrical. The groove can be defined so that the proximal end of the lead has a pre-determined orientation within the lead connector, for example, the lead can be insertable from only one side such that each channel corresponds to a pre-determined neurostimulation electrode of the lead when the clip is closed on the proximal end of the lead. In various embodiments, the clip includes a graphical representation viewable by a user that indicates a desired position and/or orientation of the proximal end of the lead within the clip so as to assist a user in placement of the proximal end of the lead within the clip.

In various embodiments, the multichannel clip is adapted for use with a four electrode neurostimulation lead, the plurality of electrical contacts including four electrical contacts corresponding to four separate channels for testing of the four electrode neurostimulation lead with the programming device.

In another aspect, the multichannel test clip includes a pair of jaws that are pivotally coupled and movable between an open position in which a distal portion of each of the jaws are spaced apart and a closed position in which the jaws secure a proximal end of the neurostimulation lead positioned therebetween. The proximal end of the lead includes a plurality of electrical contacts corresponding to a plurality of neurostimulation electrodes on a distal portion of the lead. A plurality of electrical contacts positioned within the clip so as to electrically couple with the plurality of electrical contacts on the proximal end of the lead when secured between the pair of jaws in the closed position. The clip can include a manually operable actuator for facilitating movement of the pair of jaws between the closed position and the open position to facilitate removal of the lead from the closed position. The clip can further include a stimulation cable having a plurality of conductors extending therethrough electrically coupling the plurality of electrical contacts to a proximal cable connector. The proximal cable end connector includes a plurality of connector contacts and is configured for connection with a programming device, the plurality of conductors corresponding to the plurality of electrical contacts of the clip such that each of conductors provides a separate and independent channel between a respective distal neurostimulation electrode of the lead and the programming device.

In another aspect, the multichannel clip includes a first portion and a second portion movable relative each other between an open position in which the top and bottom portions are spaced apart and a closed position in which the top and bottom portions are urged towards each other. The open position is adapted for receiving a proximal end of the neurostimulation lead having a plurality of electrical contacts corresponding to a plurality of neurostimulation electrodes on a distal portion of the lead. The closed position is adapted for securing the proximal end of the lead between the first and second portions. The clip includes a plurality of electrical contacts positioned so as to electrically couple with the plurality of electrical contacts on the proximal end of the lead when secured between the first and second portions in the closed position. The clip can further include a stimulation cable having a plurality of conductors extending therethrough electrically coupling the plurality of electrical contacts to a proximal cable connector. The proximal cable connector includes a plurality of connector contacts and is configured for electrically coupling with a programming device to allow verification and/or testing of each of the distal neurostimulation electrodes with the programming device when coupled to the connector. In various embodiments, the clip includes a manually operable actuation mechanism that effects movement of the first and second portions relative each other when in the closed position to facilitate release of the proximal portion of the neurostimulation lead from the clip.

Such devices and methods allow for more accurate and objective positioning, programming, and configuration of implantable neurostimulation electrode leads. The present invention has particular application to sacral nerve stimulation treatment systems configured to treat bladder and bowel dysfunctions. It will be appreciated however that the present invention may also be utilized in various other treatment system, or in non-medical applications. Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIGS. 5A-5D show several views of a multichannel clip in accordance with various embodiments.

FIGS. 8A-1, 8A-2, 8A-3 and 8B schematically illustrate workflows for using a clinician programmer in placing the neurostimulation leads and programming the implanted neurostimulation lead, in accordance with aspects of the invention FIG. 9 schematically illustrates a nerve stimulation system setup for neural localization and lead implantation that utilizes a control unit with a stimulation clip, ground patches, two electromyography sensor patch sets, and ground patch sets connected during the operation of placing a trial or permanent neurostimulation system, in accordance with various embodiments.

FIGS. 11A-11L illustrate curves of R-values of the electrodes used to determine distance of the electrodes from the target nerve to facilitate placement of the lead, in accordance with various embodiments.

DETAILED DESCRIPTION OF THE INVENTION

Figure 1:
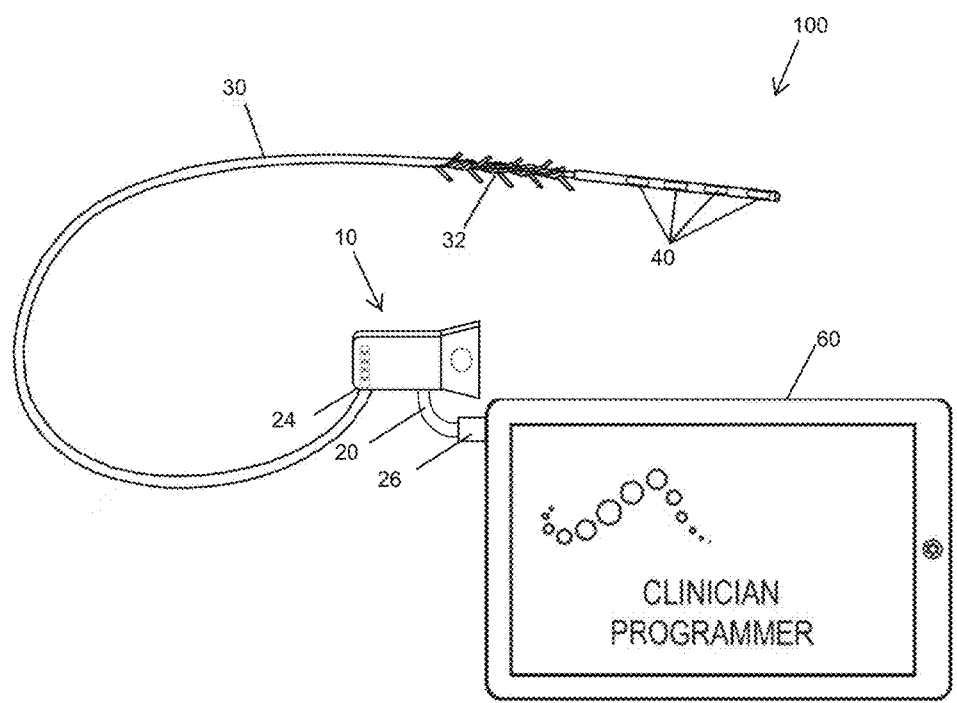
FIG. 1 schematically illustrates a nerve stimulation system, which includes a multichannel clip coupling a clinician programmer with a neurostimulation lead, in accordance with various embodiments.

The present invention relates to devices, systems and methods of testing and/or verifying electrical components of a first device with a second device. In particular, the invention relates to a multichannel clip adapted for connecting a plurality of electrical components of a first device to a second device for testing of the electrical components via multiple separate channels provided by the clip.

In various embodiments, the invention relates to a multichannel clip adapted for coupling multiple neurostimulation electrodes of an implantable lead with a clinician programming device to enable multichannel lead continuation verification and testing stimulation of the neurostimulation electrodes. In one aspect, an object of the invention is to enable multichannel lead continuity verification and test stimulation during the lead placement procedure.

In various embodiments, the multichannel clip is adapted for use in testing and/or verification of an implantable neurostimulation lead by an external programming or testing device coupled to the lead via the multichannel clip. In certain aspects, the multichannel clip is configured with multiple channels extending between a first connector coupled with the first device and a second connector coupleable with the second device through which the electrical components can be stimulated and measured individually, concurrently or in a rapid sequence. Such a configuration allows for rapid testing and/or verification of the electrical components by the second device in any number of ways, as desired by the user. For example, by use of a such a test clip, the electrical components can be tested and/or verifying individually in a rapid sequence, concurrently or in any combination, as desired. In addition, the entire testing or verification procedure can be readily repeated by use of such a clip without requiring modifying of the clip between each procedure such that an iterative process, such as placement of the lead, can be performed more quickly and efficiently and with improved accuracy, since the integrity of the channels between the electrical components and the second device remain unchanged during the iterative process.

In one aspect, the multichannel clip is a spring loaded clip having a plurality of contact points arranged so as to correspond with electrical contacts on the proximal end of a neurostimulation lead when secured within the clip. In various embodiments, the number of contact points correspond to the number of neurostimulation leads provided on the lead. In another aspect, the spring loaded clip is in communication with a programming device or other similar apparatus that performs continuity and/or test stimulation verification. Communication may be by direct wired connection or may optionally be performed wirelessly.

In a further aspect, a multichannel clip in accordance with various embodiments allows testing and verification of a plurality of electrodes (including test stimulation) to be performed by using multiplexing, by using multiple independent channels, or by using a single programmer channel. Such a configuration allows a clinician to deliver stimulations and/or measure associated electrical characteristics of electrical components coupled to a testing/programming device in a rapid sequence, concurrently, or in varying combinations, as desired.

In a further aspect, the test clip is positionable over a proximal end of a neurostimulation lead having certain conditions to be verified. Multichannel clip is in a state of communication with a programming device. Once connection is established between the stimulation lead and programmer via the test clip, evaluation may proceed. Evaluation can include basic electrical continuity for each electrode, electrode positioning evaluation (via impedance, EMG, patient responses, and the like), and test stimulation to establish useful therapeutic parameters.

In a further aspect, such systems can utilize stimulation system software configured to recognize, test, and evaluate the plurality of electrodes, including stimulation parameters, without the need to position the test clip beyond its initial placement in contact with the proximal end of the stimulation lead. Such software can be embedded in a memory of circuitry on board the clip or can be readily accessed by a programming device based on a unique identifier (e.g. make, model) associated with the multichannel clip, which can be readily accessed by the programming device upon electrical connection with the clip.

I. System Overview

FIG. 1 depicts an overview of a system 100 that allows for improved testing or verification of neurostimulation electrodes in a neurostimulation treatment system, in accordance with various embodiments. System 100 includes a neurostimulation lead 30 having a plurality of neurostimulation electrodes 40 on a distal portion that are each electrically coupled with a clinician programming device 60 through a separate channel of multichannel clip 10. As described herein, multichannel clip 10 can be referred to a test clip, stimulation clip, or stimulation cable. Multichannel test clip 10 includes multiple conductors (not shown) extending between a lead connector 24 adapted for coupling with neurostimulation lead 30 and a proximal connector 26 adapted for coupling with a clinician programming device 60.

In this embodiment, multichannel test clip 10 is a four-channel stimulation clip adapted for use in testing and/or verification of a four electrode neurostimulation lead 30. Neurostimulation lead 30 includes four neurostimulation electrodes 40 on a distal portion of the lead and a deployable anchor 32 disposed on the lead just proximal of the electrodes so as to anchor neurostimulation electrodes 40 in a target tissue of a patient once lead placement is determined. Typically, anchor 32 is not deployed until after lead 30 is placed.

Lead connector 24 is adapted to clip onto a proximal portion of lead 30 having four electrical contacts, each corresponding to a different electrode of the distal neurostimulation electrodes 40. Proximal connector 26 is adapted to couple with a testing or programming device, such as clinician programmer 60. Each of lead connector 24 and proximal connector 26 includes four corresponding electrical contacts electrically coupled via separate conductors that define four separate channels. The four channels can extend through a stimulation cable 20 of multichannel clip 10 so as to improve ease of use of and flexibility of movement during a lead placement procedure when multichannel clip 10 electrically couples neurostimulation lead 30 to clinician programmer 60.

II. Application in Neuromodulation System Configuration

Such devices, system and methods are particularly useful in testing and/or verification of neurostimulation electrodes of a neurostimulation lead in situ with a clinician programming device, as shown in FIG. 1. These devices and methods are especially applicable to sacral nerve stimulation treatment systems configured to treat bladder dysfunctions, including overactive bladder ("OAB"), as well as fecal dysfunctions and relieve symptoms associated therewith. Such treatments benefit greatly from precise positioning of the neurostimulation lead to target stimulation of the sacral nerve. For ease of description, multichannel clips are described for use in configuring neurostimulation systems for treatment of OAB. It will be appreciated however that the present invention may also be utilized for testing and/or verification in systems suited for a variety of neuromodulation uses, such as bowel disorders (e.g., fecal incontinence, fecal frequency, fecal urgency, and/or fecal retention), the treatment of pain or other indications, such as movement or affective disorders, as will be appreciated by one of skill in the art.

Sacral Neuromodulation (SNM) is an established therapy that provides a safe, effective, reversible, and long-lasting treatment option for the management of urge incontinence, urgency-frequency, and non-obstructive urinary retention. SNM therapy involves the use of mild electrical pulses to stimulate the sacral nerves located in the lower back. Electrodes are placed next to a sacral nerve, usually at the S3 level, by inserting the electrode leads into the corresponding foramen of the sacrum. The electrodes are inserted subcutaneously and are subsequently attached to an implantable pulse generator (IPG). The safety and effectiveness of SNM for the treatment of OAB, including durability at five years for both urge incontinence and urgency-frequency patients, is supported by multiple studies and is well-documented. SNM has also been approved to treat chronic fecal incontinence in patients who have failed or are not candidates for more conservative treatments.

A. Implantation of Neuromodulation System

The spinal cord is a long, thin bundle of nerves and support cells that extend from the brainstem along the cervical cord. Upon exiting the spinal cord, the nerve fibers split into multiple branches that innervate various muscles and organs transmitting impulses of sensation and control between the brain and the organs and muscles. Since certain nerves may include branches that innervate certain organs, such as the bladder, and branches that innervate certain muscles of the leg and foot, stimulation of the nerve at or near the nerve root near the spinal cord can stimulate the nerve branch that innervate the targeted organ, which may also result in muscle responses associated with the stimulation of the other nerve branch. By monitoring for certain muscle responses, either visually, through the use of EMG as described or both, the physician can determine whether the targeted nerve is being stimulated.

In one such example treatment, the neurostimulation lead is advanced through the foramen until the neurostimulation electrodes are positioned at the anterior sacral nerve root, while the anchoring portion of the lead proximal of the stimulation electrodes are generally disposed dorsal of the sacral foramen through which the lead passes at or near one of the S1-S5 nerves of the lower sacrum. The S3 sacral nerve is of particular interest for treatment of bladder related dysfunction, and in particular OAB.

Currently, SNM qualification has a trial phase, and is followed if successful by a permanent implant. The trial phase is a test stimulation period where the patient is allowed to evaluate whether the therapy is effective. Typically, there are two techniques that are utilized to perform the test stimulation. The first is an office-based procedure termed the Percutaneous Nerve Evaluation (PNE) and the other is a staged trial.

In the PNE, a foramen needle is typically used first to identify the optimal stimulation location, usually at the S3 level, and to evaluate the integrity of the sacral nerves. Motor and sensory responses are used to verify correct needle placement. A temporary stimulation lead (a unipolar electrode) is then placed near the sacral nerve under local anesthesia and is then connected to an external pulse generator (EPG) taped onto the skin of the patient during a trial phase. The stimulation level can be adjusted to provide an optimal comfort level for the particular patient. If the PNE trial is positive, the temporary trial lead is removed and a permanent quadri-polar tined lead is implanted along with an IPG under general anesthesia.

A staged trial involves the implantation of the permanent quadri-polar tined stimulation lead into the patient from the start. It also requires the use of a foramen needle to identify the nerve and optimal stimulation location. The lead is implanted near the S3 sacral nerve and is connected to an EPG via a lead extension. This procedure is performed under fluoroscopic guidance in an operating room and under local or general anesthesia. The EPG is adjusted to provide an optimal comfort level for the patient and the patient monitors his or her voiding for up to two weeks. If the patient obtains meaningful symptom improvement, he or she is considered a suitable candidate for permanent implantation of the IPG under general anesthesia, typically in the upper buttock area, as shown in FIGS. 1 and 3A.

B. EMG Assisted Neurostimulation Lead Placement

While conventional sacral nerve stimulation approaches have shown efficacy in treatment of bladder and bowel related dysfunctions, there exists a need to improve positioning of the neurostimulation leads and consistency between the trial and permanent implantation positions of the lead as well as to improve methods of programming. Neurostimulation relies on consistently delivering therapeutic stimulation from a pulse generator, via one or more neurostimulation electrodes, to particular nerves or targeted regions. The neurostimulation electrodes are provided on a distal end of an implantable lead that can be advanced through a tunnel formed in patient tissue. It is desirable for the physician to confirm that the patient has desired motor and/or sensory responses before implanting an IPG. For at least some treatments (including treatments of at least some forms of urinary and/or fecal dysfunction), demonstrating appropriate motor responses may be highly beneficial for accurate and objective lead placement.

Placement and calibration of the neurostimulation electrodes and implantable leads sufficiently close to specific nerves can be beneficial for the efficacy of treatment. Accordingly, aspects and embodiments of the present disclosure are directed to aiding and refining the accuracy and precision of neurostimulation electrode placement. Further, aspects and embodiments of the present disclosure are directed to aiding and refining protocols for setting therapeutic treatment signal parameters for a stimulation program implemented through implanted neurostimulation electrodes.

Prior to implantation of the permanent device, patients may undergo an initial testing phase to estimate potential response to treatment. As discussed above, PNE may be done under local anesthesia, using a test needle to identify the appropriate sacral nerve(s) according to a subjective sensory response by the patient. Other testing procedures can involve a two-stage surgical procedure, where a quadripolar tined lead is implanted for a testing phase (Stage 1) to determine if patients show a sufficient reduction in symptom frequency, and if appropriate, proceeding to the permanent surgical implantation of a neuromodulation device. For testing phases and permanent implantation, determining the location of lead placement can be dependent on subjective qualitative analysis by either or both of a patient or a physician.

Determination of whether or not an implantable lead and neurostimulation electrode is located in a desired or correct location can be accomplished through use of electromyography ("EMG"), also known as surface electromyography. EMG provides an objective and quantitative means by which to standardize placement of implantable leads and neurostimulation electrodes, reducing the subjective assessment of patient sensory responses.

In some approaches, positional titration procedures may optionally be based in part on a paresthesia or pain-based subjective response from a patient. In contrast, EMG triggers a measurable and discrete muscular reaction. As the efficacy of treatment often relies on precise placement of the neurostimulation electrodes at target tissue locations and the consistent, repeatable delivery of neurostimulation therapy, using an objective EMG measurement can substantially improve the utility and success of SNM treatment. The measurable muscular reaction can be a partial or a complete muscular contraction, including a response below the triggering of an observable motor response depending on the stimulation of the target muscle.

III. Example System Setups

Figure 2:
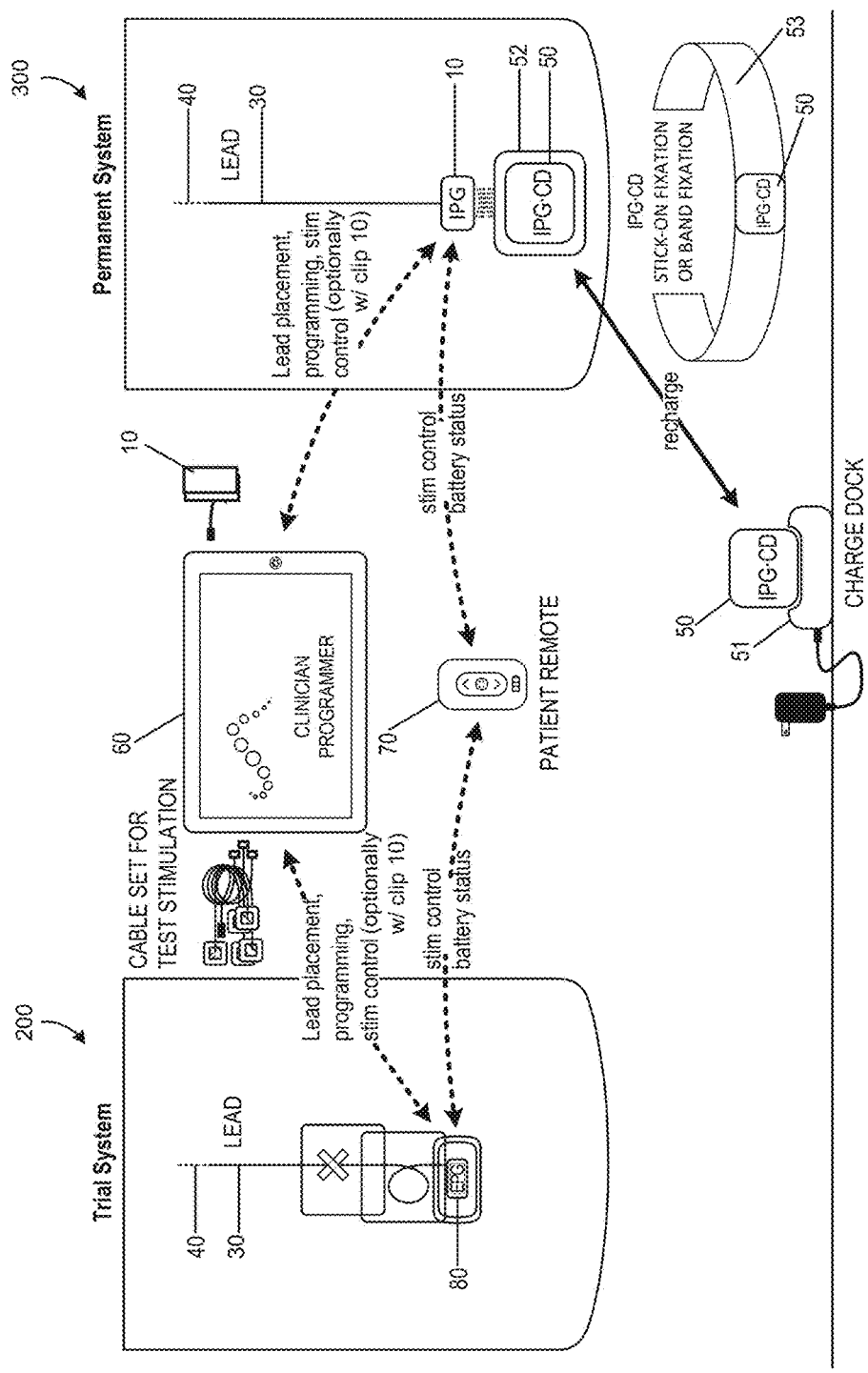
FIG. 2 schematically illustrates nerve stimulation system, which includes a clinician programmer and a patient remote used in positioning and/or programming of both a trial neurostimulation system and a permanently implanted neurostimulation system by use of a multichannel clip, in accordance with various embodiments.

FIG. 2 schematically illustrates example nerve stimulation system setups, which includes a setup for use in a trial neurostimulation system 200 and a setup for use in a permanently implanted neurostimulation system 300, in accordance with various embodiments. The EPG 80 and IPG 50 are each compatible with and wirelessly communicate with a clinician programmer (CP) 60 and a patient remote 70, which are used in positioning and/or programming the trial neurostimulation system 200 and/or permanently implanted system 300 after a successful trial. As discussed above, the system utilizes a cable set and EMG sensor patches in the trial system setup 200 to facilitate lead placement and neurostimulation programming. CP can include specialized software, specialized hardware, and/or both, to aid in lead placement, programming, re-programming, stimulation control, and/or parameter setting. This approach also allows for an almost seamless transition between the trial system and the permanent system.

In one aspect, the CP 60 is used by a physician to adjust the settings of the EPG and/or IPG while the lead is implanted within the patient. The CP can be a tablet computer used by the clinician to program the IPG, or to control the EPG during the trial period. The CP can also include capability to record stimulation-induced electromyograms to facilitate lead placement and programming.

In another aspect, the CP 60 has a control unit which can include a microprocessor and specialized computer-code instructions for implementing methods and systems for use by a physician in deploying the treatment system and setting up treatment parameters. The CP generally includes a graphical user interface, an EMG module, an EMG input that can couple to an EMG output stimulation cable, an EMG stimulation signal generator, and a stimulation power source. The stimulation cable can further be configured to couple to any or all of an access device (e.g., a foramen needle), a treatment lead of the system, or the like. The EMG input may be configured to be coupled with one or more sensory patch electrode(s) for attachment to the skin of the patient adjacent a muscle (e.g., a muscle enervated by a target nerve). Other connectors of the CP may be configured for coupling with an electrical ground or ground patch, an electrical pulse generator (e.g., an EPG or an IPG), or the like. As noted above, the CP can include a module with hardware and computer-code to execute EMG analysis, where the module can be a component of the control unit microprocessor, a pre-processing unit coupled to or in-line with the stimulation and/or sensory cables, or the like.

In other aspects, the CP 60 allows the clinician to read the impedance of each electrode contact whenever the lead is connected to an EPG, an IPG or a CP to ensure reliable connection is made and the lead is intact. This may be used as an initial step in both positioning the lead and in programming the leads to ensure the electrodes are properly functioning. The CP is configured to operate in combination with an EPG when placing leads in a patient body as well with the IPG during programming. The CP can be electronically coupled to the EPG during test simulation through a specialized cable set or through wireless communication, thereby allowing the CP to configure, modify, or otherwise program the electrodes on the leads connected to the EPG. The CP may also include physical on/off buttons to turn the CP on and off and/or to turn stimulation on and off.

Once the neurostimulation lead is placed and a temporary or permanent system is in place, electrical pulses generated by the EPG and IPG are delivered to one or more targeted nerves via one or more neurostimulation electrodes at or near a distal end of each of one or more leads. The leads can have a variety of shapes, can be a variety of sizes, and can be made from a variety of materials, which size, shape, and materials can be tailored to the specific treatment application. While in this embodiment, the lead is of a suitable size and length to extend from the IPG and through one of the foramen of the sacrum to a targeted sacral nerve, in various other applications, the leads may be, for example, implanted in a peripheral portion of the patient's body, such as in the arms or legs, and can be configured to deliver electrical pulses to the peripheral nerve such as may be used to relieve chronic pain. It is appreciated that the neurostimulation leads may vary according to the nerves being targeted and that the multichannel clip described herein can be modified as needed for use with a particular lead.

Figure 3:
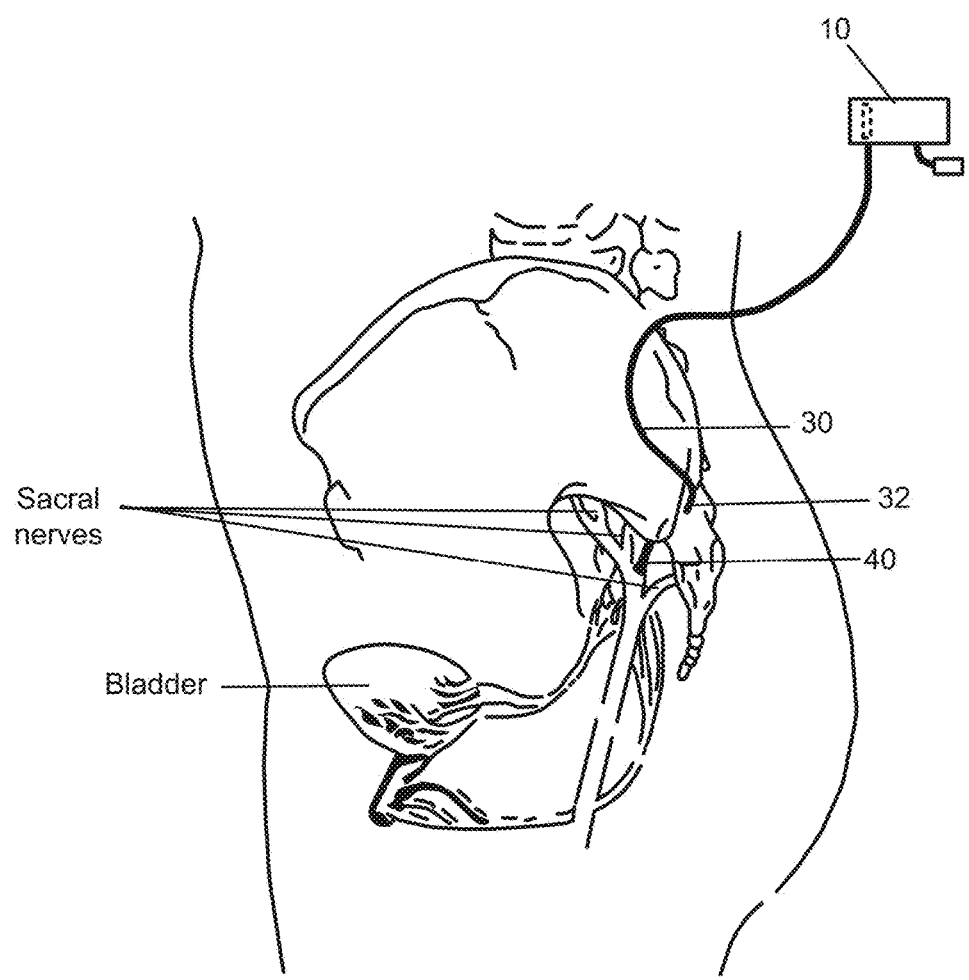
FIG. 3 shows an example of a neurostimulation system having a partly implanted stimulation lead that is coupled with a multichannel clip device to testing of neurostimulation electrodes in situ, in accordance with various embodiments.

FIG. 3 schematically illustrates an example of multichannel clip 10 coupled with a partly implanted neurostimulation lead 30 extending through the S3 foramen for stimulation of the S3 sacral nerve with neurostimulation electrodes 40. Once coupled to neurostimulation lead 30, multichannel clip 10 can be connected to clinician programmer (not shown) to facilitate testing and/or verification to ensure proper placement of lead 30 at the targeted sacral nerve. Such placement can be verified by measuring and/or observing EMG responses during stimulation of each neurostimulation electrodes 40, as described in further detail below. Once the lead is placed by use of multichannel clip 10, the neurostimulation lead can be connected to an EPG for use in a trial or an IPG implanted in a lower back region and connected to a neurostimulation lead extending through the S3 foramen for stimulation of the S3 sacral nerve.

IV. Example Multichannel Clip Devices

Figure 5D:
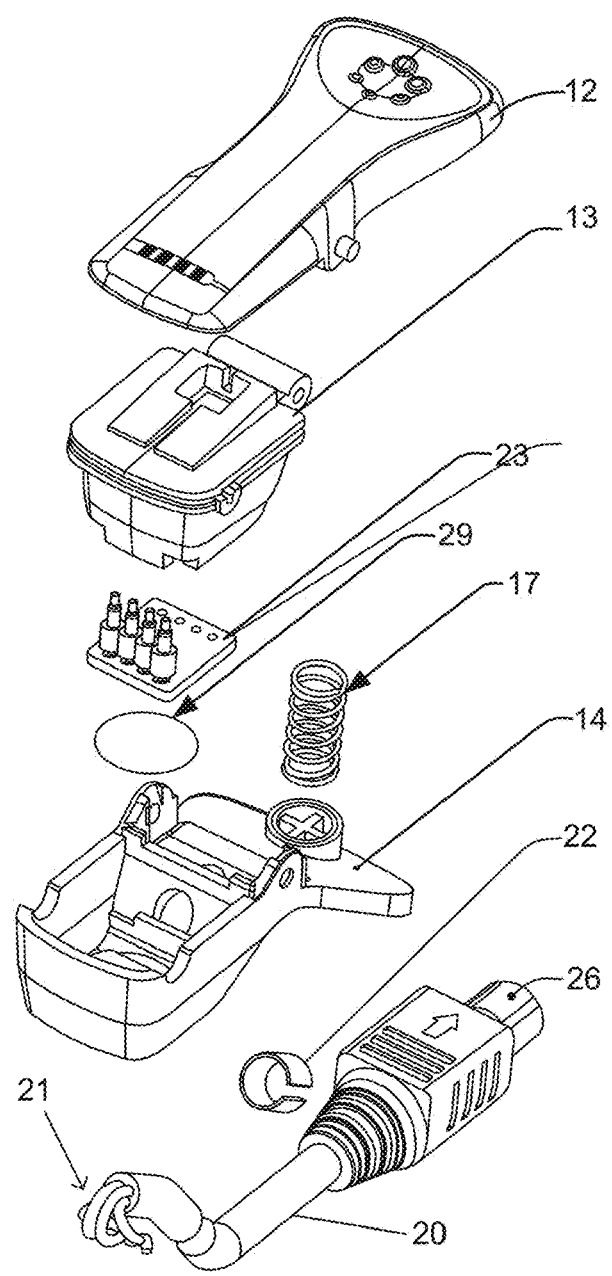

FIG. 5A-5C show detail views of an example multichannel clip 10 and its various components, shown also in an exploded view in FIG. 5D. Multichannel clip 10 includes a lead connector 24 having multiple connector contacts 25 that are each electrically coupled to corresponding connector contacts 27 in a proximal connector 26 through separate channels. In this embodiment, multichannel clip 10 is a four-channel stimulation clip. Multichannel clip 10 typically includes a spring loaded clip with a lead connector 24 is disposed along an inside of a pair of jaws of the clip. Lead connector 24 includes four electrical connector contacts 25 that are electrically coupled through four separate channels to four corresponding connector contacts 27 in proximal connector 26. Lead connector 24 is adapted for electrically coupling to electrical contacts on a proximal portion of neurostimulation lead 30 that correspond to a set of multiple neurostimulation electrodes 40 on a distal portion thereof, while proximal connector 26 is adapted for connecting to a testing or programming device, such as a clinician programmer 60.

In this embodiment, multichannel clip 10 includes a pair of opposing members 12, 14 that are pivotally coupled to one another at a pivotal coupling 15 and a lead connector 24 disposed along an inside surface between opposing members 12, 14. Movable members can include a top member 12 and a bottom member 14, each member having a proximal portion defining a handle and distal portion defining a jaw on opposite sides of the pivotal coupling 15. The pair of opposing members 12, 14 are manually operable between a closed position in which distal opposing jaws are moved towards each other so as to securely engage a portion of the lead 30 within clip 10 and an open position in which distal opposing jaws are spaced apart so as to receive the portion of the lead 30 within lead connector 24. An urging member, such as spring 17, extending between movable members 12, 14 urges the opposing distal jaw portions toward the closed position with sufficient force to retain the lead 30 grasped within clip 10 and maintain electrical connectivity between electrical contacts of the lead 30 and lead connector 24. Manually pressing together proximal portions of movable members 12, 14 increases separation of distal portions of members 12, 14 so as to receive the proximal portion of lead 30 therein within lead connector 24. One or both of movable members 12, 14 can include a distal portion that is adapted to improve ease of use in manually operating the clip. For example, in this embodiment, an enlarged handle portion of top member 12 includes a thumb gripping surface 16 having a thumb depression and a ring of tactile gripping dots (e.g. textured, rubberized).

Lead connector 24 includes multiple connector contacts 25 arranged to electrically couple with multiple electrical contacts on a proximal portion of lead 30 when secured between opposing members 12, 14 of clip 10. The electrical contacts on the proximal portion of lead 30 correspond to the distal neurostimulation electrodes 40. The multiple connector contacts are positioned and arranged so as to concurrently couple with the respective corresponding electrical contacts on the lead 30 so as to establish multiple channels concurrently through which stimulations can be delivered in any sequence or combination, as desired for testing or verification. In this embodiment, connector contacts of lead connector 24 extend from a printed circuit board (PCB) assembly 23 disposed within a portion of bottom member 14. PCB assembly 23 can be coupled to bottom member 14 by an adhesive disk 29.

Proximal connector 26 includes multiple electrical connector contacts 27 corresponding to the multiple channels provided by clip 10. In this embodiment, proximal connector 26 is configured to readily connect directly to clinician programmer 60 via a connector receptacle 66, as shown in FIG. 6B. Proximal connector 26 is configured as a circular connector plug having multiple connector pins contacts 27 that are configured to be received within a corresponding connector receptacle 66 of the clinician programmer. Advantageously, proximal connector 26 can be configured in accordance with an accepted standard to allow for ready connection with a corresponding standard connector type of the clinician programmer (e.g. ODU Mini-Snap). While a cylindrical connector plug is depicted here, it is appreciated that proximal connector 26 could be configured according to various other standards (e.g. USB, etc.) or non-standard connector types. In some embodiments, proximal connector 26 can include an adapter to allow for ready connection between differing types of connectors in various testing and/or programming devices, as desired.

In this embodiment, each of the connector contacts 27 is coupled to corresponding connector contacts of a PCB assembly 23 through multiple corresponding conductors (e.g. wires) 20. Typically, corresponding conductors 20 are insulated wires that extend to connector 26 through a stimulation cable 20. In various embodiments, stimulation cable 20 extends a short distance (e.g. ranging from 1 to 12 inches) so as to allow the clinician freedom to move the clinician programmer 60 relative the proximal portion of the lead 30 secured within multichannel clip 10. This is particularly useful in a testing or verification process that may necessitate adjustment of the neurostimulation lead 30 while the clinician views testing or verification data displayed on a handheld clinician programming device 60 or is observed by a clinician. Such is the case in a lead placement procedure. Clip 10 can include a ferrule 22 where stimulation cable 20 exits the bottom member 14 so as to stiffen the portion of stimulation cable 20 and better withstand stresses and fatigue associated with repeated movement of the proximal connector 26 relative the clip 10.

In this embodiment, multichannel clip 10 further includes a connector holder 13 between the distal portions of movable members that defines a receptacle of lead connector 24 in which the proximal portion of lead 30 is received and defines and supports the components of the lead connector 24, as detailed further below in FIG. 6A. Connector holder 13 is disposed along an inside between the distal jaw portions of the opposing members 12, 14 and can include corresponding top and bottom members that are pivotally coupled. PCB assembly 23 can be secured to a bottom member of connector holder 13. In one aspect, connector holder 13 can be configured to fittingly receive a particular lead 30.

Figure 6A:
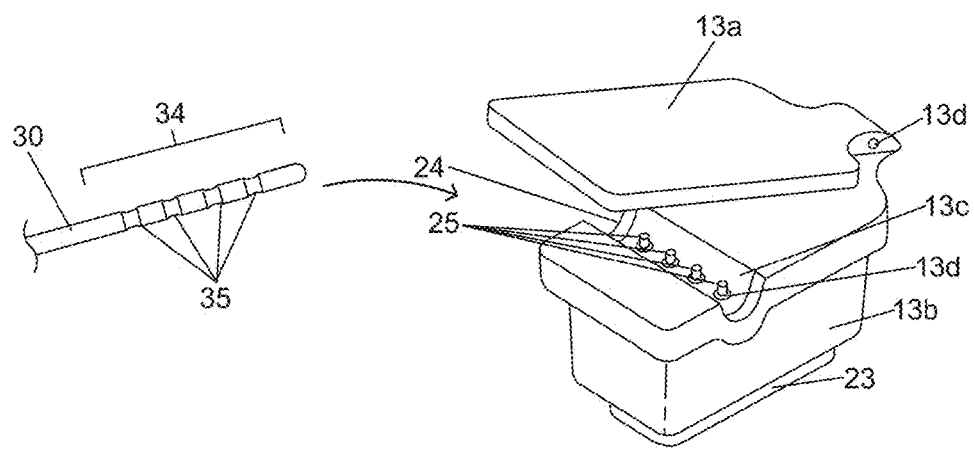
FIGS. 6A-6B show detail view of a lead connector of a multichannel clip adapted for connecting to a neurostimulation lead and a proximal connector of the clip adapted for connecting with a clinician programmer, in accordance with various embodiments.
Figure 6B:
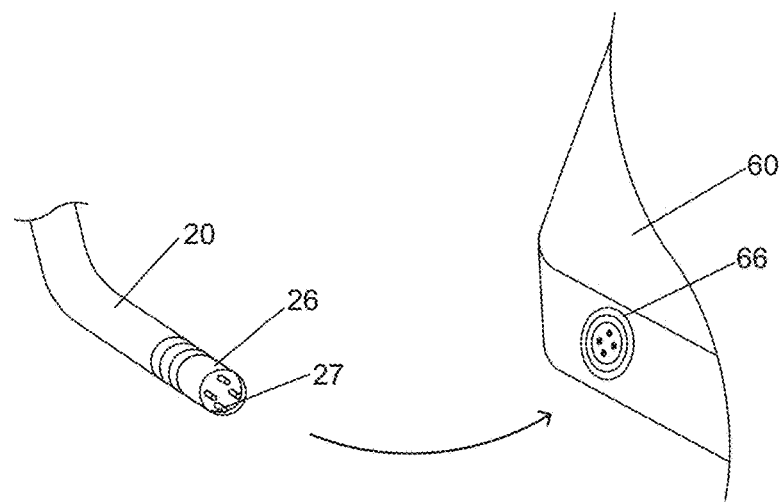

FIGS. 6A-6B show detail views of each of the lead connector 24 within connector holder 13 and proximal connector 26 as well as the corresponding connecting portions of the lead 30 and the programming device 60. The lead connector 24 is shown without the pair of opposing members 12, 14 and associated components for improved visibility of connector holder 13. While each of the connectors in this embodiment illustrate four electrical contacts that correspond to four separate channels for testing and/or verification of a lead having four neurostimulation electrodes, it is appreciated that the respective could be configured to define any number of channels. For example, clip 10 could be configured to define fewer channels, such as two or three channels, or configured to define more channels, such as five channels or more, as needed for a particular application.

In some embodiments, clip 10 could be configured with multiple lead connectors electrically coupled to a single proximal connector, so as to be suitable for use in testing and/or verification of a neurostimulation system having multiple leads.

As can be seen in FIG. 6A, lead connector 24 is configured to receive a proximal connection portion 34 of neurostimulation lead 30, which includes four electrical contacts 35. Each electrical contact 35 corresponds to a different electrode of the distal neurostimulation electrodes 40. In this embodiment, each of the neurostimulation electrical contacts 35 is defined as a cylindrical electrode band having a concave outside surface that facilitates engagement with corresponding electrical contacts within clip 10, as well as contacts in a header portion of an IPG or EPG. Lead connector 24 can be defined with a receptacle that receives proximal connection portion 35. In this embodiment, connector holder 13 includes an upper jaw 13a and a lower jaw 13b that are movably connected by a pivotal coupling 13d. Upper jaw 13a operably engages with top opposing member 12 and lower jaw 13b engages with bottom opposing member 14, respectively, such that when movement of distal jaw portions of movable members 12, 14 toward one another causes upper and lower jaws 13a, 13b to clamp or clip onto the portion of lead 30 when received within lead connector 24. In some embodiments, upper jaw 13a is attached to top member 12 while lower jaw 13b is attached to lower member 13b such that separating distal portions of movable members 12, 14, in turn, separates upper and lower jaws 13a, 13b to allow placement of lead 30 within lead connector 24. While connector holder 13 is depicted as a separate component coupled to the pair of opposing members, it is appreciated that the connector holder could be incorporated into the pair of opposing members in some embodiments.

In various embodiments, the receptacle of connector 24 is defined within connector holder 13, which also supports various other components of connector 24. Receptacle can be defines as a groove 13c within one or both of upper and lower jaws 13a, 13b dimensioned to receive the proximal connection portion 35 of lead 30. Connector holder can further include a plurality of holes 13d disposed within the receptacle through which the plurality of connector contacts 25 extend into the groove receptacle so as to electrically engage corresponding electrical contact bands on the proximal portion of lead 30 when clipped within lead connector 24. PCB assembly 23 can be coupled to an underside of lower connector holder 13b. While connector holder 13, along with PCB assembly 23 defines lead connector 24, the pair of movable members 12, 14 provides a clamping force via urging member 17 sufficient to engage electrical contacts 35 of lead 30 with electrical contacts 25 within lead connector and to retain proximal connecting portion 34 of lead 30 within lead connector 24. Retention of lead 30 within lead connector 24 can be provided in part by engagement of the electrical contacts 25 within the concave recess of the electrical contacts 35. In various other embodiments, additional retention features, such as color, or interfacing features (e.g. pins and holes) can be used to provide further retention of proximal connecting portion 34 within lead connector 24.

As can be seen in FIG. 6B, proximal connector 26 can be defined as a cylindrical connector plug with multiple electrical contact pins 27 adapted to be received within a corresponding cylindrical connector receptacle 66 of the testing/programming device 60. In this embodiment, proximal connector 26 is configured as an ODU Mini-Snap cylindrical connector plug with at least four electrical connector pins that correspond to the four channels provided by clip 10. This type of connector utilizes a snap feature to retain the connector plug within the connect receptacle 66 and maintain the integrity of the electrical connection during testing and/or programming.

In various embodiments, each of lead connector 24 and proximal connector 26 are permanently and fixedly attached to the conductors 21 that define the multiple channels through the clip. Such a configuration provides a more robust and dependable electrical connection as compared to conventional methods that require manually connecting J-clips or alligator to electrical contacts of the lead, which could inadvertently become detached when the programming device is handled by the clinician. Such a configuration further improves ease of use as it does not require repeated adjustment and separate attachment of each electrical connection. Maintaining consistency and integrity of the electrical connection and improving ease of use is particularly important in methods where electrode testing and verification must be repeated multiple times, as is the case during a lead placement procedure.

In one aspect, a body of clip 10 can be formed of a suitable electrically insulating material, for example a polymeric material, so as to ensure the conductive channels provided by clip 10 remain separate from one another.

In yet another aspect, the lead connector 24 can be defined so that the proximal portion of the lead only fits in a pre-determined orientation. In this embodiment, the receptacle is defined to receive the proximal portion of the lead 30 in a single orientation, as shown by the arrow in FIG. 5B. Such a configuration helps ensure that the channels provided by stimulation clip 10 correspond to certain pre-determined neurostimulation electrodes of lead 30. For example, in this embodiment, by configuring lead connector 24 to interface with the proximal portion of lead 30 in only one orientation, this ensures that pin #1 of a four pin proximal connector corresponds to neurostimulation lead #1 of lead 30. It is appreciated that such a pre-determined orientation would depend on the particular configurations of the device being coupled via the multichannel clip.

In various embodiments, multichannel clip 10 includes a graphical indicator 11 to assist the clinician in connecting the proximal portion of the lead within lead connector 24 in the proper location and orientation within clip 10. In this embodiment, graphical indicator 11 is shown as a graphical representation of the proximal portion 34 of lead 30 on an outer surface of top opposing member 12 so as to readily viewable by the clinician during attachment to the lead 30. It can be appreciated, however, that various other graphical indicators can be used, including but not limited to a marking, text, arrows, or lights.

While a pivoting forcep-type clip is described above, it is appreciated that such a multichannel clip could encompass alternative designs. For example, in an alternative embodiment, clip 10 could include an outer housing with an interior spring-loaded member that securely engages the proximal portion upon insertion of the lead 30 within the housing. A movable lever or button may load the spring-loaded member to displace the member and allow removal of the proximal portion of the lead, which can remain loaded until a subsequent insertion of another lead release the spring loaded member. In yet another alternative embodiment, multichannel clip could include a manual fastener that secures the proximal portion of lead in place within lead connector.

Figure 7A:
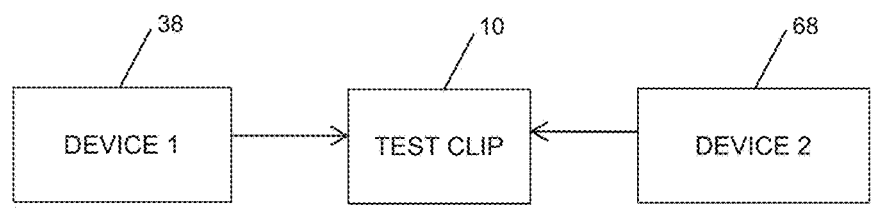
FIGS. 7A-7C illustrate schematic of testing setup configurations, in accordance with various embodiments.
Figure 7B:
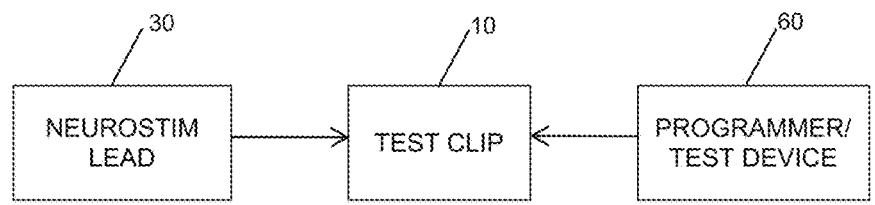
Figure 7C:
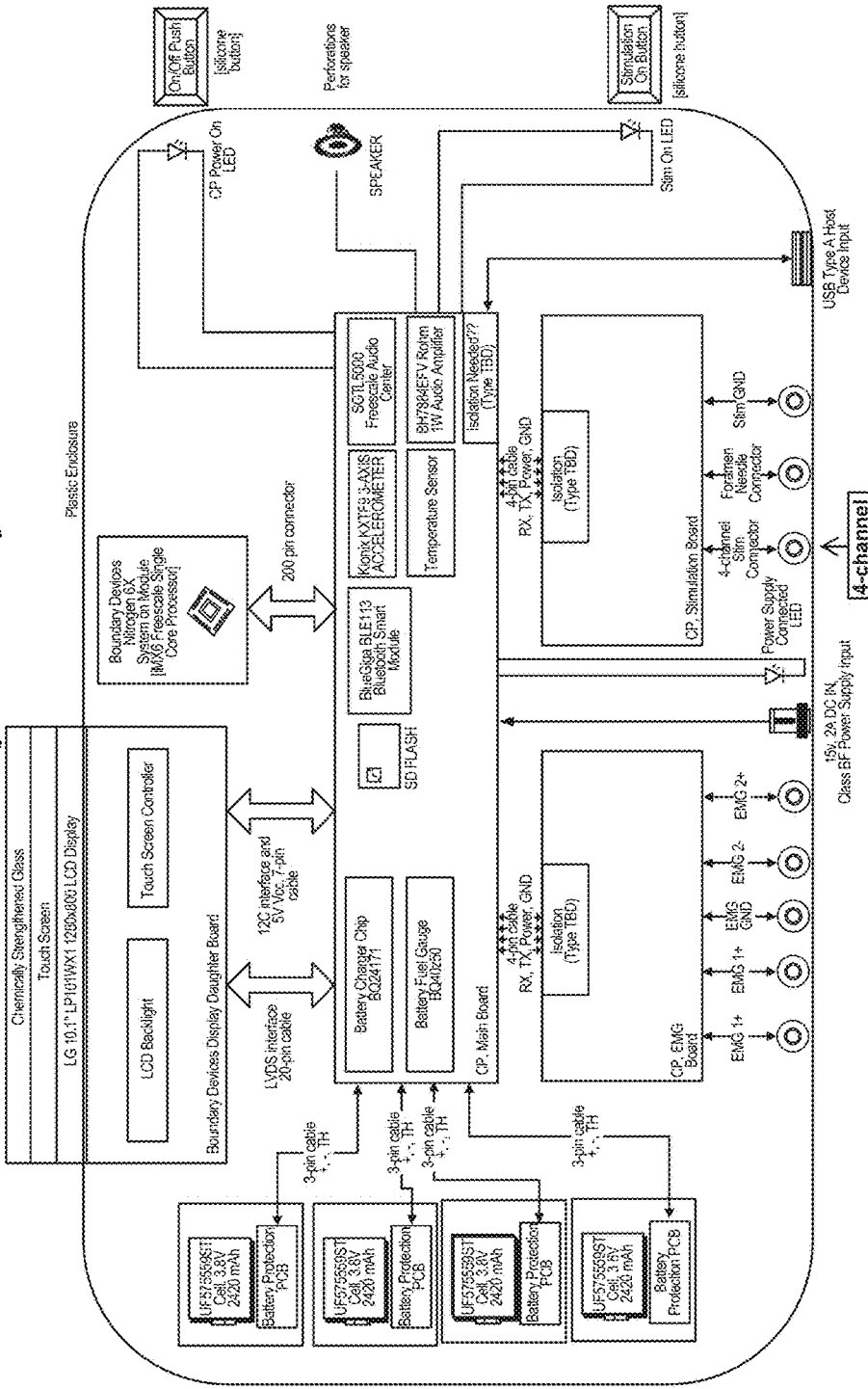

FIGS. 7A-7C illustrate schematics of setups with which multichannel clip 10 can be used. FIG. 7A illustrates use of a multichannel test clip 10 electrically coupling a multiple electrical components of a first device 38 with a second device 68 for testing, verification, or programming of the electrical components by use of the second device. The first device could include any device having multiple electrical components for which testing is desired, which could include devices used in any number of applications, including but not limited to electronics, PCB fabrication, computing, industrial, lighting, geological, biological, and various research applications. The second device 68 could include various test devices suitable for connection with such a clip, preferably a device configured for rapid delivery and/or measurement of electrical signals, such as in a sequencing or multiplexing operation. In some embodiments, the second device can further include capability for providing a data output to the user. Such a test clip 10 can include any of the features and capabilities described herein as desired for particular devices being tested or for particular applications.

7B illustrates use of a multichannel test clip 10 electrically coupling a neurostimulation lead 30 and a clinician programming device 60, as described previously. Such a configuration is particularly useful during initial testing or verification of an implanted neurostimulation lead during a lead placement procedure, but can also be used in an electrode characterization, programming or re-programming procedure, as desired.

FIG. 7C schematically illustrates a block diagram of the configuration of the CP 60 and associated interfaces and internal components. As described above, CP 60 is typically a tablet computer with software that runs on a standard operating system. The CP 60 includes a communication module, a stimulation module and an EMG sensing module. The communication module communicates with the IPG and/or EPG in the medical implant communication service frequency band for programming the IPG and/or EPG. As seen in the figure, CP 60 includes a connector by which a multichannel clip (e.g. 4 channel stim clip) can be attached. While this configuration reflects CP as a portable user interface display device, such as a tablet computer, it is appreciated that the CP may be incorporated into various other types of computing devices, such as a laptop, desktop computer, or a standalone terminal for use in a medical facility.

V. Example Use of MultiChannel Clip in Lead Placement

A. Workflows for Lead Placement with CP

Figures 1, 8A:
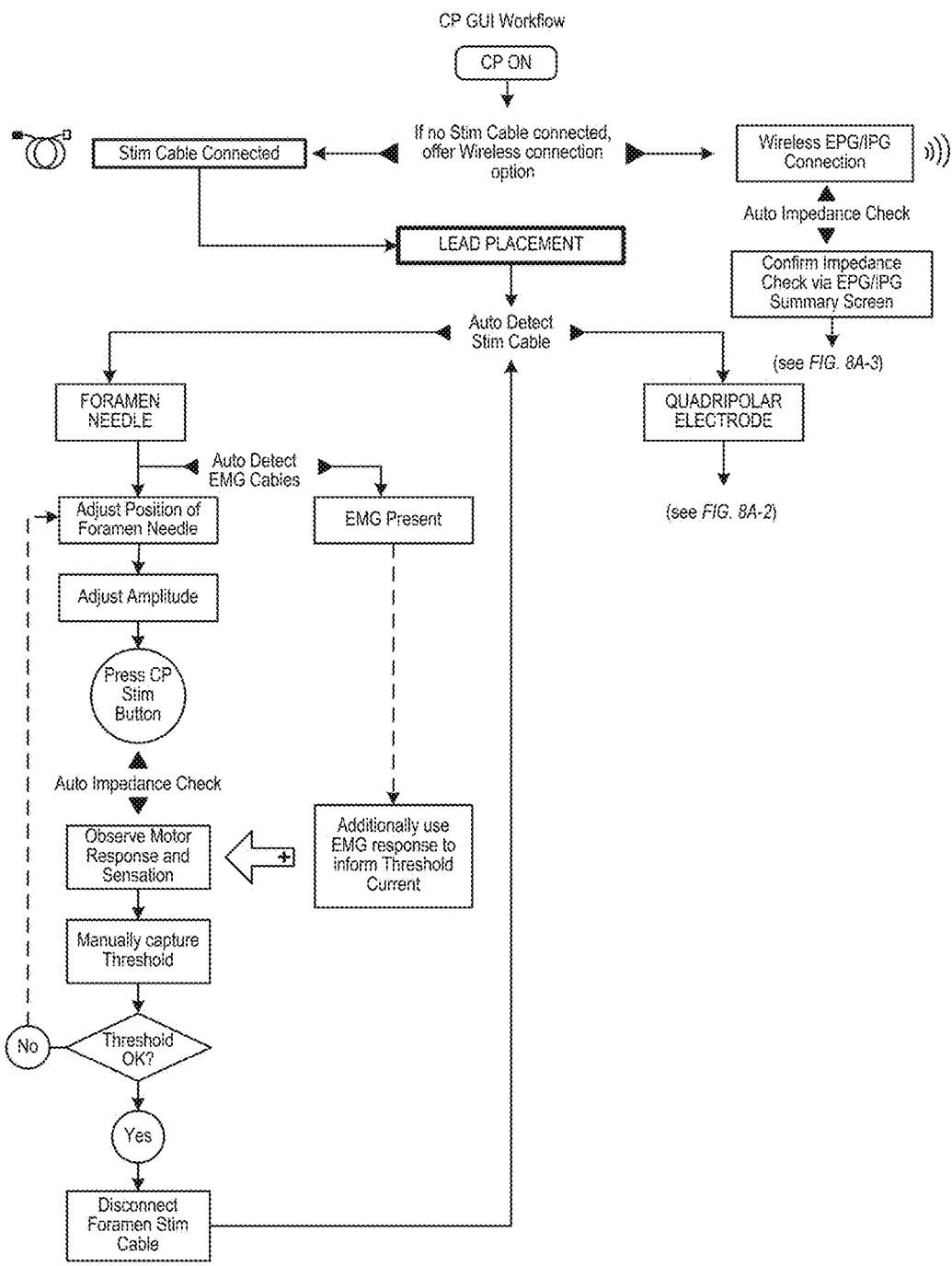
Figures 2, 8A:
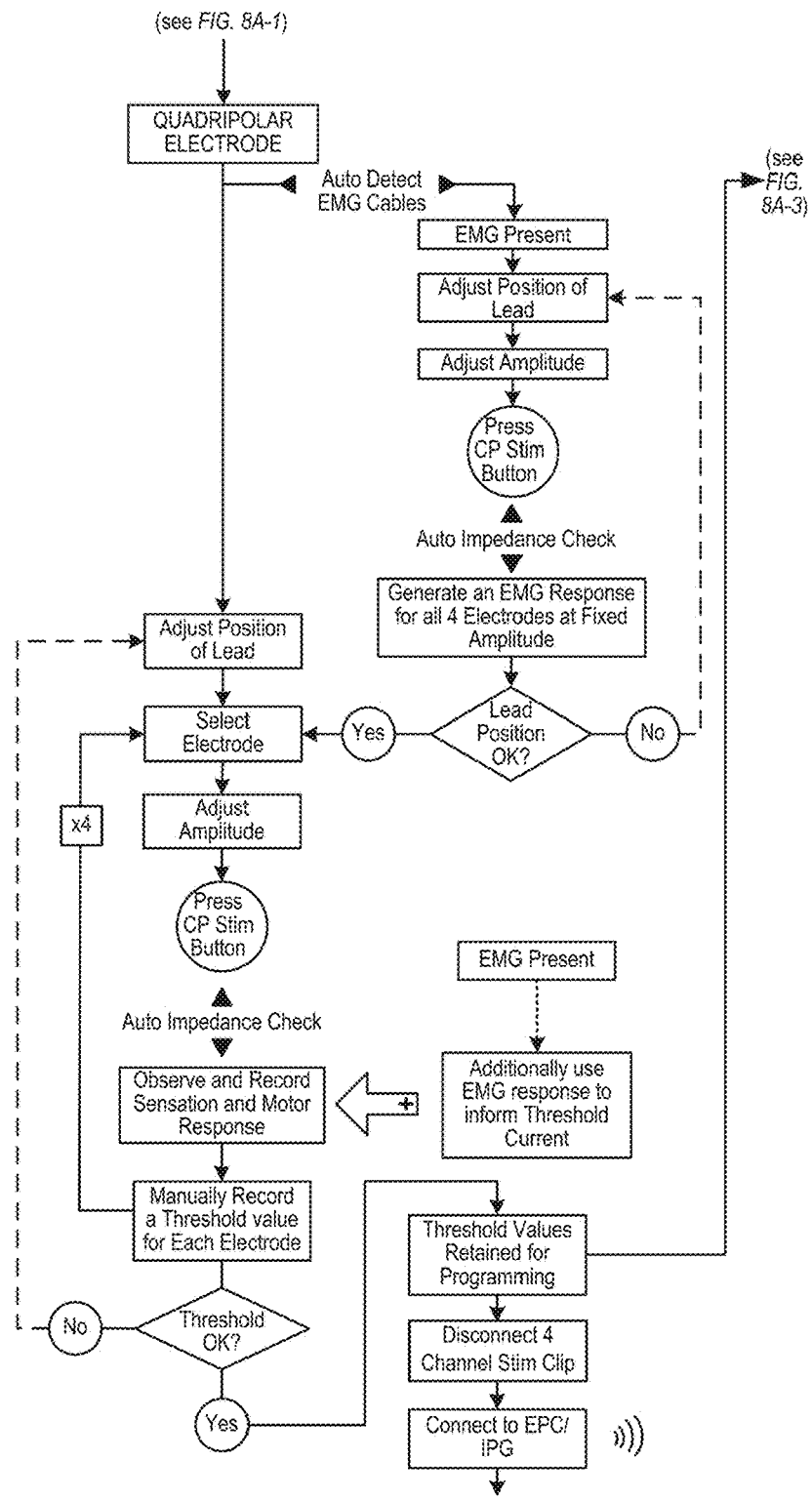
Figures 3, 8A:
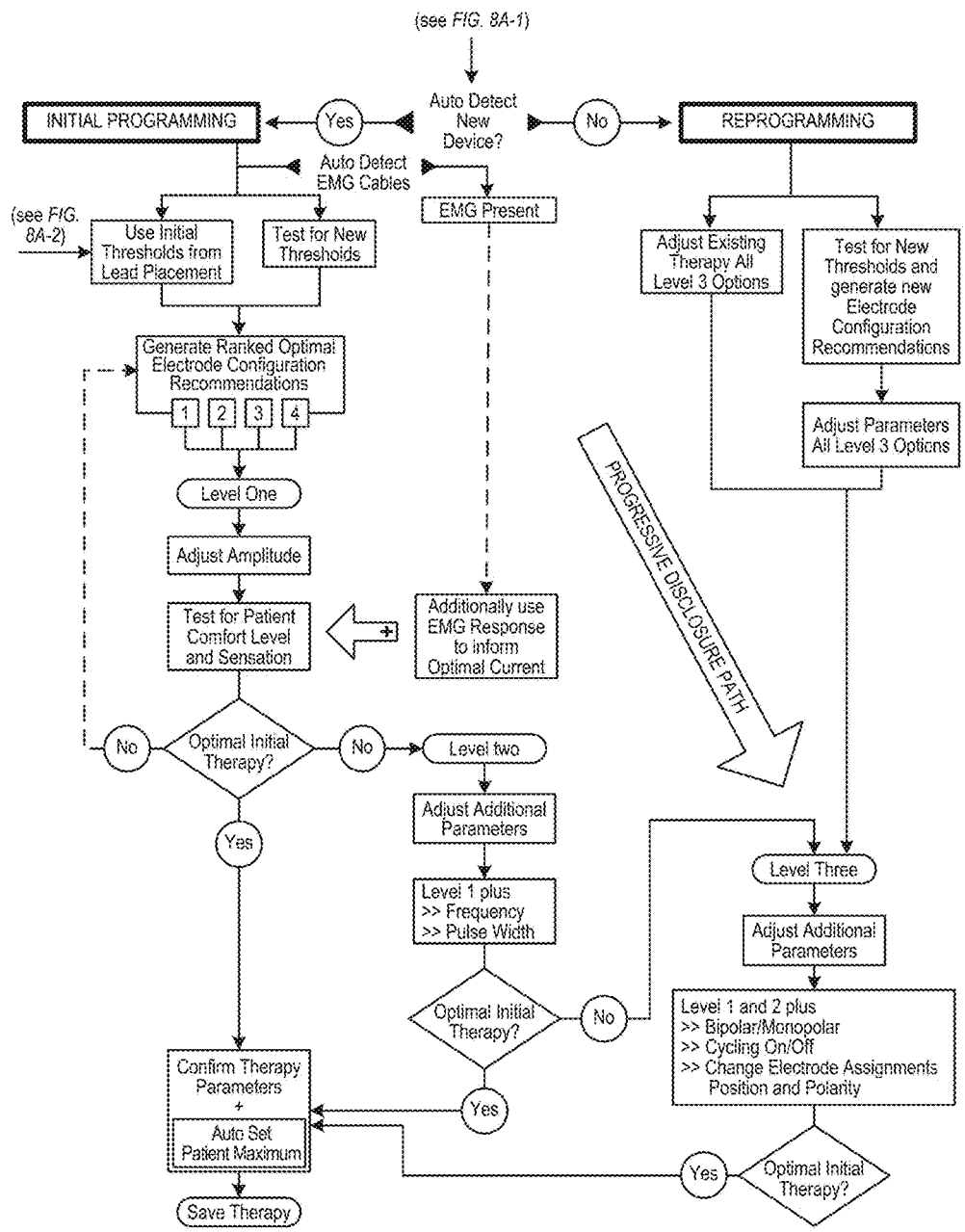
Figure 8B:
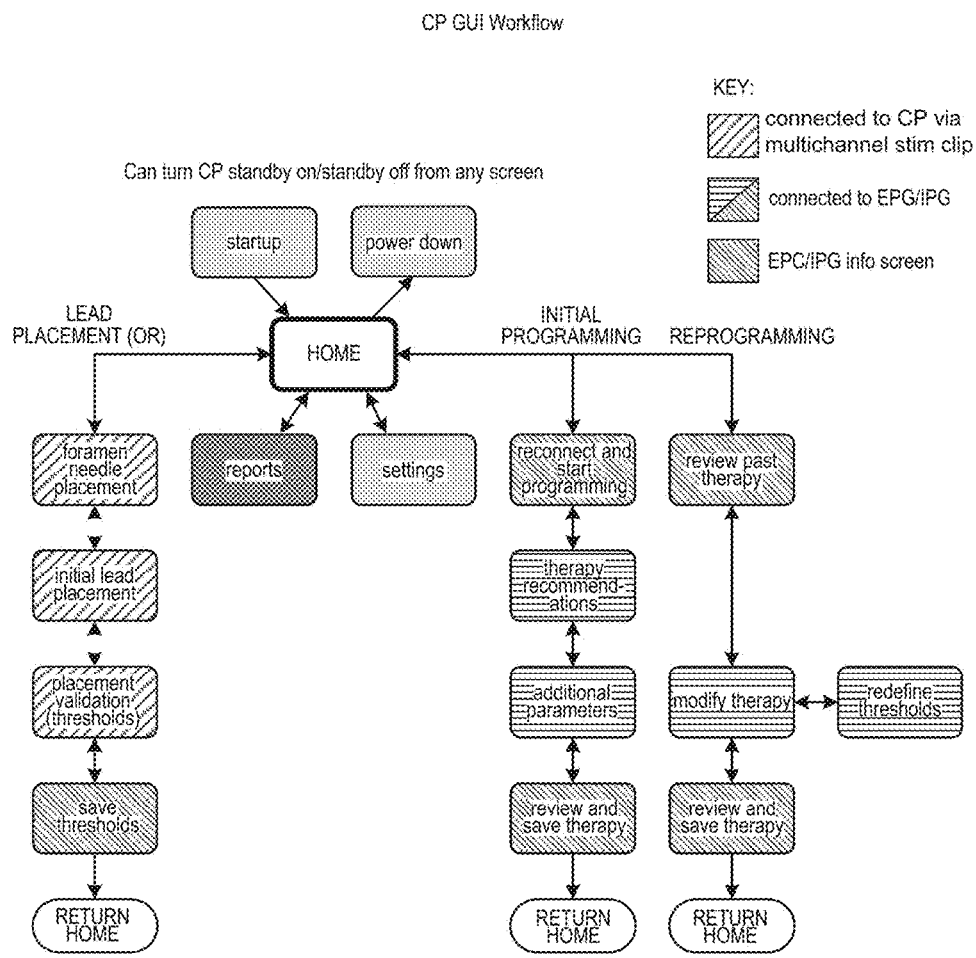

FIGS. 8A-1, 8A-2, 8A-3 and 8B illustrate schematics of the workflow used in lead placement and programming of the neurostimulation system using a CP with EMG assist, in accordance with various embodiments. FIGS. 8A-1, 8A-2 and 8A-3 schematically illustrates a detailed overview of the use of a CP having a graphical user interface for lead placement and subsequent programming, which may include initial programming and reprogramming. FIG. 8B illustrates a CP graphical user interface screen representation schematic of workflow that includes the various setups and connections associated with each step.

B. Neurostimulation Lead Placement with EMG

Placement of the neurostimulation lead requires localization of the targeted nerve and subsequent positioning of the neurostimulation lead at the target location. Typically, neural localization of the targeted nerve is performed by use of a foramen needle that is positioned at various locations and stimulated until an neuromuscular response is observed that is indicative of stimulation at the targeted nerve location.

In certain embodiments, EMG can be used to improve the accuracy and resolution of neural localization with the foramen needle as well as to improve consistency and ease of performing each of neural localization and lead placement, as well as subsequent programming of the implanted neurostimulation system. EMG sensors are placed on the patient in a manner so as to record neuromuscular responses associated with a desired muscle movement. The key responses indicative of well-placed sacral nerve stimulation for urinary and fecal dysfunctions are the "big toe response" and the "anal bellows." The big toe response is the plantar flexion of the big toe. Such an approach is made feasible by integration of EMG recording, display and analysis with the CP, which is operatively coupled with the neurostimulation lead and used during lead placement and subsequent programming. In another aspect, automation of these aspects within the CP can further reduce the duration and complexity of the procedure and improve consistency of outcomes. For example, automation of electrode threshold determinations based on EMG responses can provide rapid feedback during lead placement and to identify optimal programming parameters. These advantages are further realized by use of a multichannel clip that allows test stimulations to be repeated or sequenced in a fairly rapid fashion. It is understood that some test stimulations may require a certain brief period of time before a characteristic or a neuromuscular response can be recorded. Regardless, use of a multichannel clip allows for testing and verification in a manner considerably faster than a clinician could manually connect each individual electrical contact by a j-clip or alligator clip.

Figure 9:
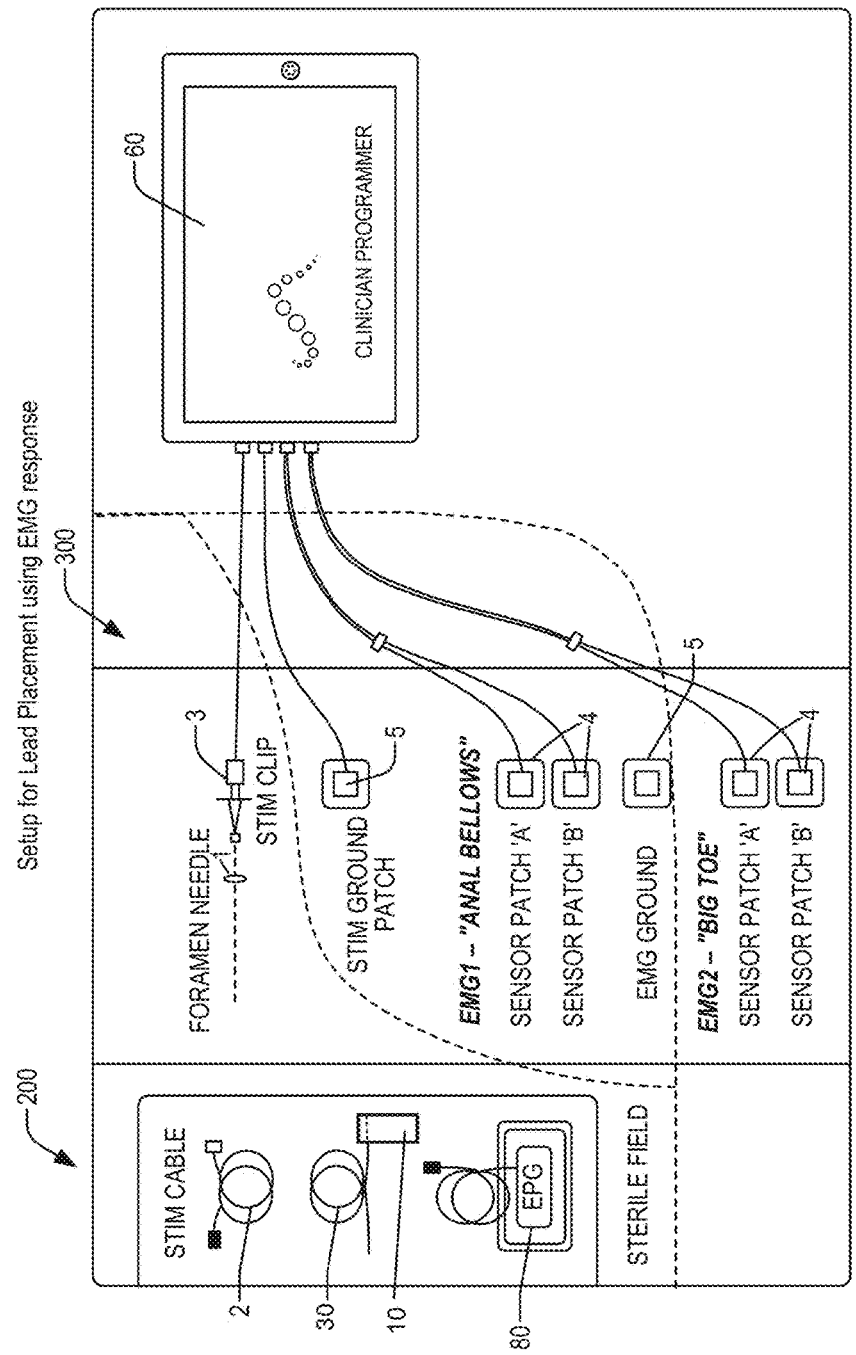

FIG. 9 illustrates a system setup for neural localization and lead placement using EMG response, as described above. As can be seen, several cable sets are connected to the CP 60. The stimulation cable set consists of one stimulation mini-clip 3 and one ground patch 5. It is used with a foramen needle 1 to locate the sacral nerve and verify the integrity of the nerve via test stimulation. Another stimulation cable set with four stimulation channels 2 is used to verify the lead position with a tined stimulation lead 20 during the staged trial. Both cable sets are sterilizable as they will be in the sterile field. A total of five over-the-shelf sensing electrode patches 4 (e.g., two sensing electrode pairs for each sensing spot and one common ground patch) are provided for EMG sensing at two different muscle groups (e.g., perineal musculature and big toe) simultaneously during the lead placement procedure. This provides the clinician with a convenient all-in-one setup via the EMG integrated CP. Typically, only one electrode set (e.g., two sensing electrodes and one ground patch) is needed for detecting an EMG signal on the big toe during an initial electrode configuration and/or re-programming session. Placement of the EMG patches on the patient for detection of an EMG waveform are shown in FIGS. 17A and 17B, which illustrate patch placement for detection of big toe response and anal bellow response, respectively.

In one aspect, the EMG signal is used to evaluate placement quality and programming quality based on stimulation amplitude to evoke a response. The EMG responses are measured based on one of several approaches for quantifying the compound muscle action potential (CMAP). In other embodiments, stimulation automatically increases until an EMG response is observed. While this electrode configuration and programming is typically conducted while the neurostimulation lead is attached to an EPG or IPG, it can also be performed by stimulating the neurostimulation lead with the CP via a multichannel clip, in accordance with aspects of the invention.

Figure 4:
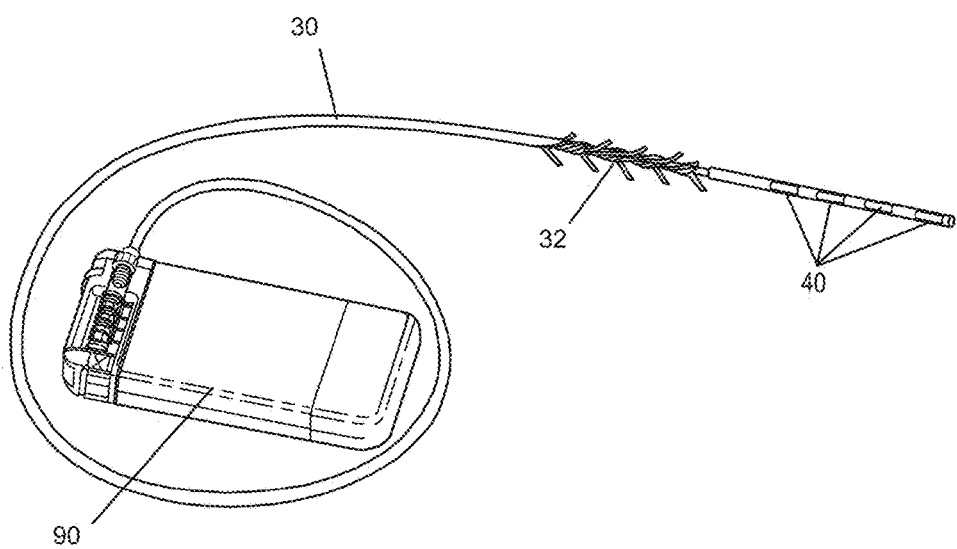
FIG. 4 shows an example of a neurostimulation system having an implantable neurostimulation system having a neurostimulation lead suitable for use with a multichannel clip, in accordance with various embodiments.
Figure 10:
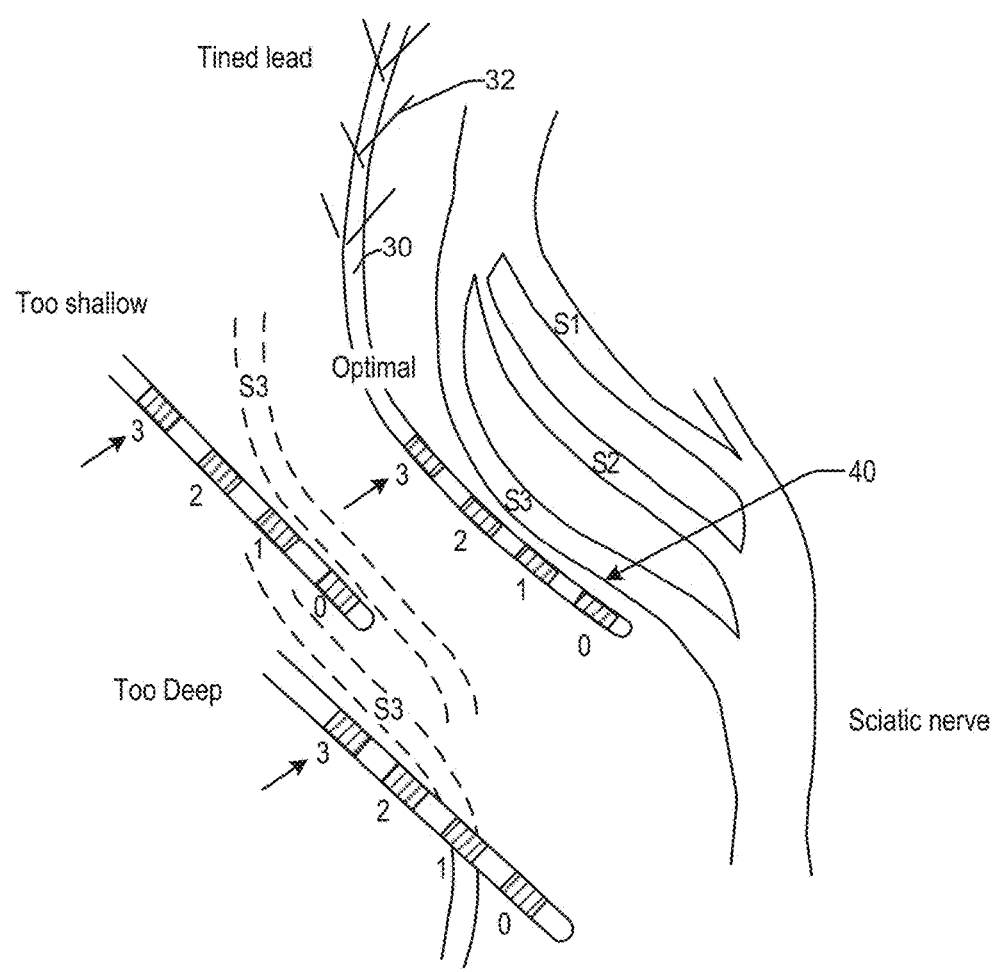
FIG. 10 illustrate differing positions of the neurostimulation lead relative the targeted nerve during placement of the lead.

After neural localization is complete, the neurostimulation lead is advanced to the target location identified during neural localization with the foramen needle. Typically, a neurostimulation lead include multiple electrodes along a distal portion of the lead, as can be seen in FIG. 4, such that there are various differing positions along which the lead can be placed at or near the target location. For example, as shown in FIG. 10, the lead can be advanced "too deep" beyond the targeted nerve, can be placed "too shallow." In another example, the lead can be tilted or angled such that the distal or proximal electrodes are spaced too far away from the target nerve. The neurostimulation lead can be re-positioned along various differing paths within the three-dimensional space of the implantation site to an optimal location and alignment by advancing or retracting the lead along the insertion axis and/or steering the lead in a lateral direction from the insertion axis as needed. While it is desirable for all four electrodes to be in an optimal location, three out of four electrodes being in acceptable proximity to the target nerve to deliver neurostimulation therapy is generally acceptable. Determining an actual location of the lead, however, can be difficult and time-consuming using conventional methods of manually adjusting the stimulation on each electrode separately and relying on observation of the muscle responses after each stimulation. Fluoroscopy is an often used tool to verify lead position against anatomical landmarks, however, this approach is not very effective since nerves are not visible under fluoroscopy.

In one aspect, the system provides improved lead placement by determining lead position of a multi-electrode lead relative the target nerve with EMG using an electrode sweeping process. This system connects the lead to the CP with a multichannel clip (e.g. a four-channel clip). The clip allows the system to energize each electrode in rapid succession without requiring separate attachment and detachment on each electrode with a J-clip or alligator slip, such as is used in convention methods. This aspect is advantageous since utilization of a J-clip or alligator clip to make contacts to tightly pitched electrode is difficult and time consuming and could potentially result in movement of the lead during testing. Thus, use of a clip as described here facilitates fine tuning of lead placement that would prove difficult without such a clip.

In the sweeping process, the system identifies a principal electrode. This may be a default selection by the system or selected by the physician using the CP. The stimulation of the principal electrode is adjusted until an adequate motor response with a maximum amplitude CMAP is obtained at which point the stimulation level or amplitude is recorded. The system then sweeps through all the remaining electrodes of the lead with the same stimulation level and records the EMG responses from each electrode. Typically, the sweeping process is performed rapidly. For example each contact can be stimulated individually at the same stimulation level for 1 second such that the entire sweeping cycle can be conducted in about 4-5 seconds for a four-electrode lead. The system can determine responses for each electrode that can be used to indicate the relative distances of each electrode from the target nerve, which may also be recorded for subsequent use in programming of the EPG or IPG. There are several options as to how this sweeping process can be used to facilitate fine tuning of lead placement, including the following two options.

Option 1: In one approach, the EMG response value for each electrode can be indicated on a graphical user interface display of the clinician programmer. For example, the response value can be indicated by color coding the electrodes on the display (see FIG. 14D) or by bars or boxes displayed next to each electrode on the Electrode Status Indicator 64 (see FIG. 12A). These indicators readily communicate the robustness of the EMG response achieved at each electrode to the clinician. In one aspect, each electrode may be assigned an R-value, where the R-value is a unit-less number, derived from each electrode's EMG peak CMAP amplitude recorded during the sweeping process, and normalized relative to that of the principal electrode selected by the clinician. In some embodiments, an R-value >0.5 is deemed a "good" location (e.g. color coded green; R-value of 1 or higher is preferable); an electrode with an R-value that is 0.25<r<0.5 is deemed "not ideal" (e.g. color coded yellow); and an electrode with an R-value that is r<0.25 is deemed not acceptable (e.g. color coded red).

Option 2: In another approach, the response value is illustrated in terms of the distance to the target nerve determined based on the relative response value of each electrode. In one aspect, the R-values may be converted to relative distance which allows for ready interpretation of a relative position of the electrode to the target nerve. Examples of these R-value and distance curves in regard to differing positions of the leads are described in FIGS. 10-11L as follows.

FIG. 10 illustrates initial placement of the neurostimulation lead 20 along the path, the lead 20 including four neurostimulation electrodes 40, electrode #0-3, from electrode #0, the distal most electrode to electrode #3, the proximal most electrode. In one aspect, the "optimal lead position" for neurostimulation treatment is one in which each of the neurostimulation electrodes 40 are adjacent the targeted nerve (e.g. S3 sacral nerve) along the electrode portion 40. If the lead is not advance far enough, the lead position is "too shallow" such that only the more proximal electrodes (e.g. 0, 1) are adjacent the targeted nerve. If the lead is advanced too far, the lead position is "too deep" such that only the more proximal electrodes (e.g. 2, 3) are adjacent the targeted nerve and the more distal electrodes have been advanced beyond the target location.

The axial position of the lead relative the target nerve can be reflected using the R-values for each electrode obtained during sweeping. If the lead is too shallow, the R-value curves obtained may resemble FIG. 11A if the R-values were keyed off of electrode #3, the most proximal electrode. This curve is converted to the distance curve shown in FIG. 11B, which indicates that electrodes #3 and #2 are unacceptably far from the target nerve. In response to this curve, in some cases, combined with fluoroscopy images (showing the relative position of lead and anatomic landmarks), the physician may determine and/or the system may suggest to the physician, such as by indicator on the CP, to insert the lead deeper. The sweeping process can be repeated and new R-value and distance curves obtained until distance curves indicate a more optimal position of the lead, such as that shown in FIG. 11C for example. If the lead is positioned "too deep", the R-value curves obtained may resemble that in FIG. 11D if the R-values were keyed off of electrode #3. The R-value curve converts to the distance curve shown in FIG. 11E, which indicates that electrodes #0 and #1 are unacceptably far from the target nerve. In response to this curve, in some cases, combined with fluoroscopy images (showing the relative position of lead and anatomic landmarks), the physician may determine and/or the system may suggest to the physician, such as by indicator on the CP, to pull the lead back. The sweeping process can then be repeated and new R-value and distance curves obtained until distance curves indicate a more optimal position of the lead, such as that shown in FIG. 11F for example.

If the lead is too shallow, the R-value curves obtained may resemble FIG. 11G if the R-values were keyed off of electrode #0, the most distal electrode. This curve is converted to the distance curve shown in FIG. 11H, which indicates that electrodes #3 and #2 are unacceptably far from the target nerve. In response to this curve, in some cases, combined with fluoroscopy images (showing the relative position of lead and anatomic landmarks), the physician may determine and/or the system may suggest to the physician, such as by indicator on the CP, to insert the lead deeper. The sweeping process can be repeated and new R-value and distance curves obtained until distance curves indicate a more optimal position of the lead, such as that shown in FIG. 11I for example. If the lead is positioned "too deep", the R-value curves obtained may resemble that in FIG. 11J if the R-values were keyed off of electrode #0. The R-value curve converts to the distance curve shown in FIG. 11K, which indicates that electrodes #2 and #3 are unacceptably close from the target nerve. In response to this curve, in some cases, combined with fluoroscopy images (showing the relative position of lead and anatomic landmarks), the physician may determine and/or the system may suggest to the physician, such as by indicator on the CP, to pull the lead back. The sweeping process can then be repeated and new R-value and distance curves obtained until distance curves indicate a more optimal position of the lead, such as that shown in FIG. 11L for example. Generally, the shape of the curves FIGS. 11A-L provide a visual representation that aid in optimal lead placement. Optimal lead placement comprises R-vales in a similar range and/or robust EMG responses at reasonable stimulation amplitudes. For example, similar R-values but low EMG responses at high stimulation amplitudes alert the clinician that the lead needs to be re-positioned closer to the target nerve region. The combination of R-values, trial and error, and fluoroscopic imaging aid in optimal lead positioning, such as axial and/or lateral adjustments of the lead.

In some embodiments, the R-value and/or distance curves may be determined by the system and used to communicate a suggestion to the clinician, such as with the CP, as to whether the lead should be advanced, retracted or steered. In other embodiments, the R-values and/or the associated curves may be displayed on a graphical user interface of the CP so as to provide a visual indicator of the robustness of each electrode and/or its relative location. In one aspect, a suitable lead position is one in which at least three of the four electrodes are disposed adjacent to and along the targeted nerve.

Figure 12A:
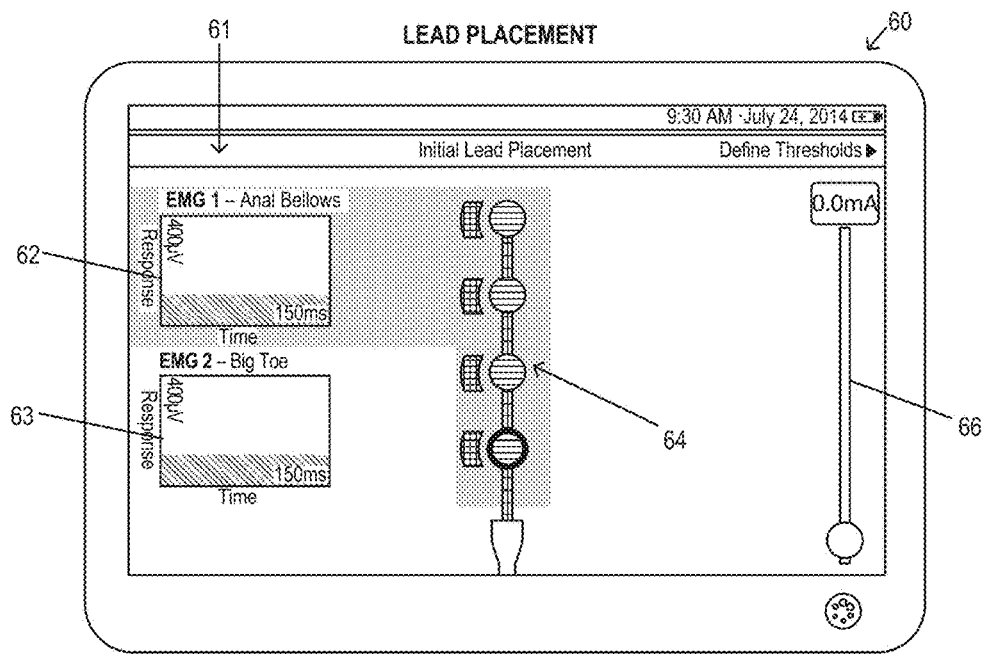
FIGS. 12A-12B illustrate a graphical user interface display of a clinician programmer during an alternative electromyography assisted neurostimulation lead placement procedure, in accordance with various embodiments.
Figure 12B:
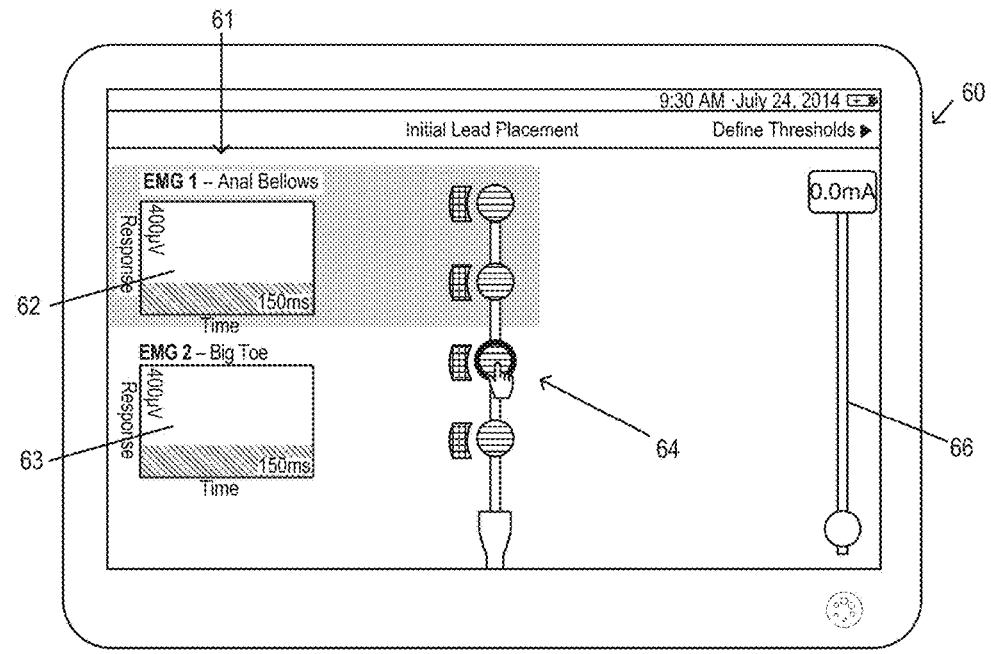

In various embodiments, as shown in FIG. 12A-12B for example, a graphical user interface of the CP 60 can be used to display electrode testing and/or verification results to a clinician during an initial lead placement procedure, in accordance with various embodiments. The CP 60 interface can include EMG waveform displays 61 used to monitor a desired neuromuscular response, an Amplitude display 66 and an Electrode Status Indicator 64, which during lead placement includes a representation of the electrode portion of the lead 20. The EMG waveform display 61 includes two waveform displays, an Anal Bellows EMG display 62, which is coupled with EMG 1 patch, and a Big Toe EMG display 63 coupled with EMG 2 patches adhered on the patient's foot. In this procedure, the EMG signal is used to evaluate placement quality based on stimulation amplitude to evoke a response. In some embodiments, the user selects the amplitude and presses "stimulate," after which each electrode is stimulated for one second. The user determines if the response amplitudes are acceptable. In other embodiments, the system automatically increases until a self-determined level is reached or until a pre-determined EMG response is recorded. In some embodiments, amplitude adjustment can be done in auto-adjusting increments, as described previously. The system may provide a suggestion as to a direction to move the lead if the responses are unacceptable. In various embodiments, the responsiveness of each electrode may be graphically represented, for example by bars or boxes to the right of each electrode in the graphical representation of the lead in the Electrode Status Indicator 64. In this example, boxes to right of each contact represent the EMG value (e.g., peak value) for that contact as follows: open square (<50 uV), 1 closed square (50-100 uV), 2 closed squares (100-150 uV), and 3 closed squares (150+uV). A visual indicator that the more distal electrodes (electrode #0, 1) have sub-optimal EMG peak values may communicate to the clinician that the lead needs to be pulled back proximally until at least three of the four electrodes, preferably all electrodes, have acceptable EMG peak values (e.g. 3 closed square at 150+uV).

After selection of a principal electrode, the CP performs a test stimulation on the 4-channel lead via the multichannel clip, which is typically a quick check across all electrodes of the lead (e.g., sweep). In one aspect, the CP records the EMG waveform displays 62 and 63 and the amplitude threshold reading for each selected electrode during this test stimulation. From this test stimulation, the CP 60 may display the suitability of each electrode for neurostimulation in the electrode status display 64 on the user display of the CP, for example, by a color coding or other suitable indicator. The electrode may be marginal or unsuitable for use as a cathode based on either or both of the amplitude threshold being too high or based on lack of response in the EMG. Another indicator can be provided on the user display of the CP that communicates to the clinician that the lead needs to be advanced distally. After adjustment of the lead by the clinician, the process can be repeated until at least three of the four electrodes have green indications to denote optimal positioning. Clearly, a method that relies on an iterative process for fine-tuning placement of the neurostimulation lead is advanced by use of a multichannel clip that allow the relative positions of the electrodes relative the target tissue area to be determined and/or verified in a relatively rapid manner.

C. Validation of Lead Placement

In another aspect, the CP can validate lead placement by testing for stimulation thresholds for each electrode of the four channel lead. The CP increases the stimulation level of the selected electrode and records the magnitude of the EMG response, which can appears in the EMG waveform displays 61 on the graphical user interface of the CP 60. The stimulation is increased until a pre-determined or desired EMG response threshold is reached, at which point the amplitude is recorded and displayed on the electrode status display 64 next to the subject electrode. Optionally, the response for each electrode can be characterized at this time and recorded for use in subsequent programming. The above process is repeated for each electrode. If the threshold amplitude is outside a suitable range of amplitude thresholds, the amplitude may be designated as marginal or unsuitable for use as a cathode in neurostimulation. Designations may be made by visual indicators, such as color coding (e.g. green, orange, red) to indicate suitability of the selected electrode for use as a cathode in a neurostimulation treatment.

In one aspect, the CP 60 connects to the EPG/IPG and establishes communication, which may be indicated on the graphical user interface as well. The CP can obtain and review EPG/IPG device info and record the stimulation levels on the EPG/IPG and/or associate the EPG/IPG with the recorded stimulation levels. The graphical user interface may include a Threshold Detail Display that displays a summary of EMG motor responses, as well as recorded sensory responses and amplitude thresholds.

In order to confirm correct lead placement, it is desirable for the physician to confirm that the patient has both adequate motor and sensory responses before transitioning the patient into the staged trial phase or implanting the permanent IPG. However, sensory response is a subjective evaluation and may not always be available, such as when the patient is under general anesthesia. Experiments have shown that demonstrating appropriate motor responses is advantageous for accurate placement, even if sensory responses are available. As discussed above, EMG is a tool which records electrical activity of skeletal muscles. This sensing feature provides an objective criterion for the clinician to determine if the sacral nerve stimulation results in adequate motor response rather than relying solely on subjective sensory criteria. EMG can be used not only to verify optimal lead position during lead placement, but also to provide a standardized and more accurate approach to determine electrode thresholds, which in turn provides quantitative information supporting electrode selection for subsequent determinations of electrode recommendation and programming, discussed in further detail below. Using EMG to verify activation of motor responses can further improve the lead placement performance of less experienced operators and allow such physicians to perform lead placement with confidence and greater accuracy. Advantageously, as the positioning and programming functionality are integrated in many embodiments of the clinician programmer, at least some of the validation thresholds may be correlated to the subsequent stimulation programming, so that (for example) positioning is validated for a particular programming protocol to be used with that patient. Regardless, stimulation programming protocols may employ EMG data obtained during lead positioning or validation to more efficiently derive suitable neurostimulation treatment parameters for that patient.

Figure 13:
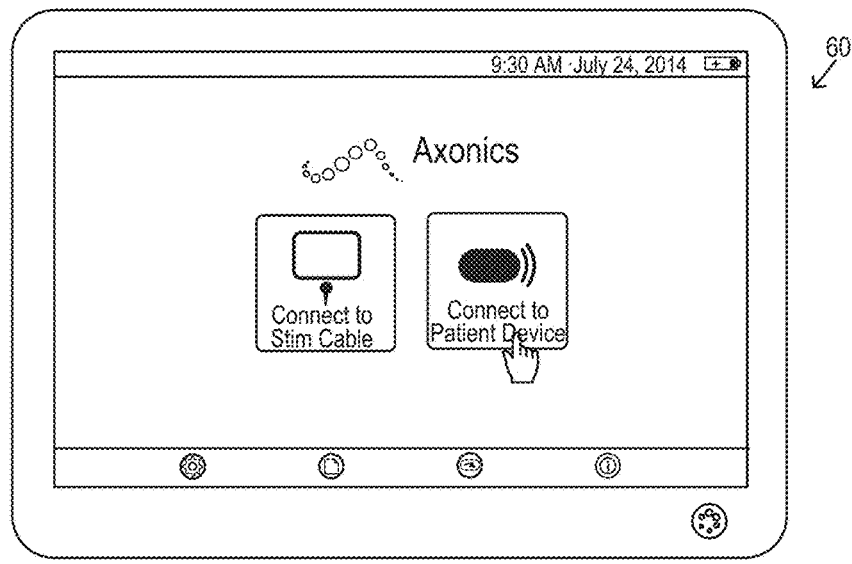
FIG. 13 illustrate a graphical user interface display of a clinician programmer during an alternative electromyography assisted neurostimulation lead placement procedure, in accordance with various embodiments.

FIG. 13 depicts a graphical user interface display of the CP 60 that allows the clinician to select whether the CP is connected to neurostimulation lead 30 via multichannel test clip or wirelessly through the IPG or EPG coupled to the lead 30. The physician can also confirm this by viewing the device info in subsequent screens displayed on the CP. In various figures and sections herein, multichannel clip 10 is referred to as Stim Clip or Stim Cable, which appears in the user interface in of CP in FIG. 13.

VI. Example Methods of Use

Figure 14:
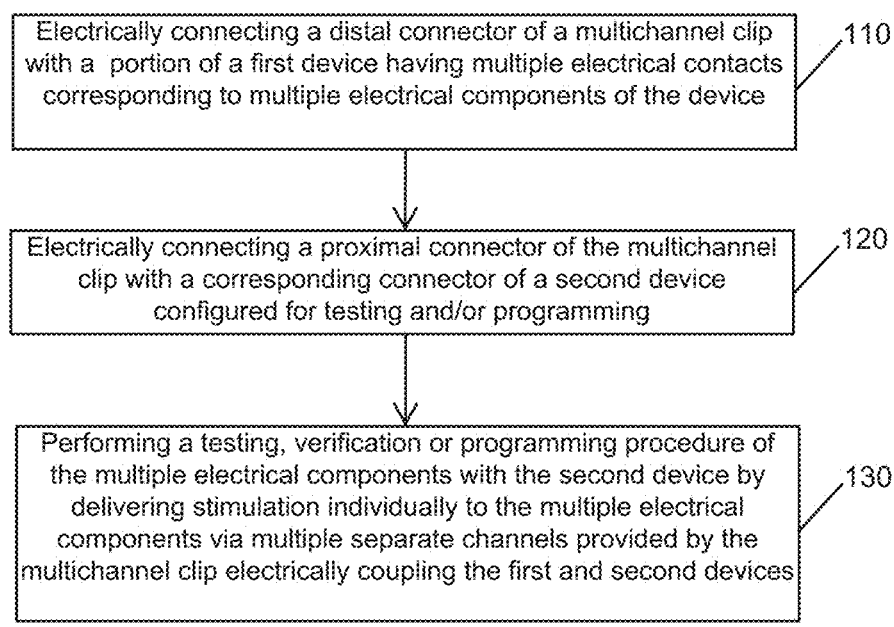
FIGS. 14-16 illustrate methods of using a multichannel clip in accordance with embodiments of the invention.
Figure 15:
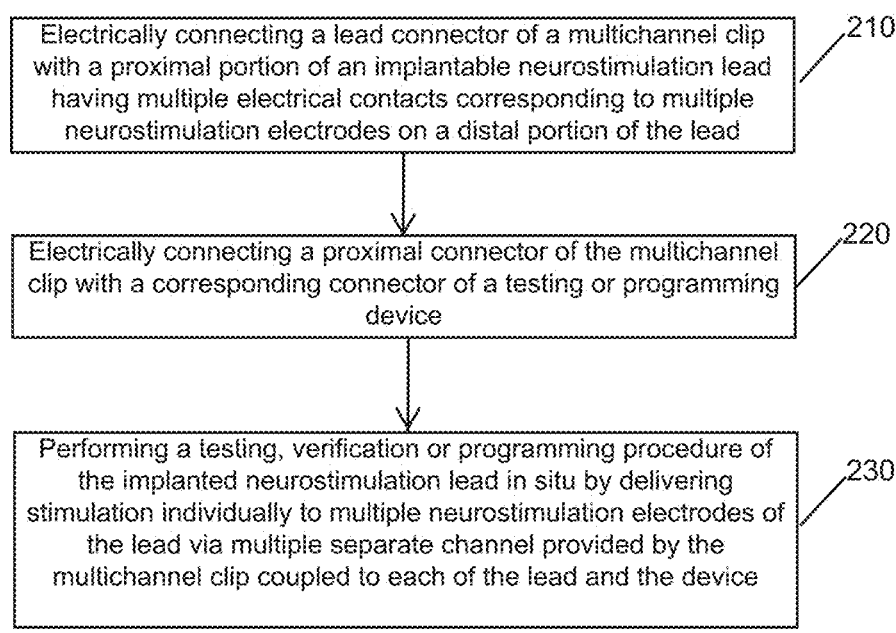
Figure 16:
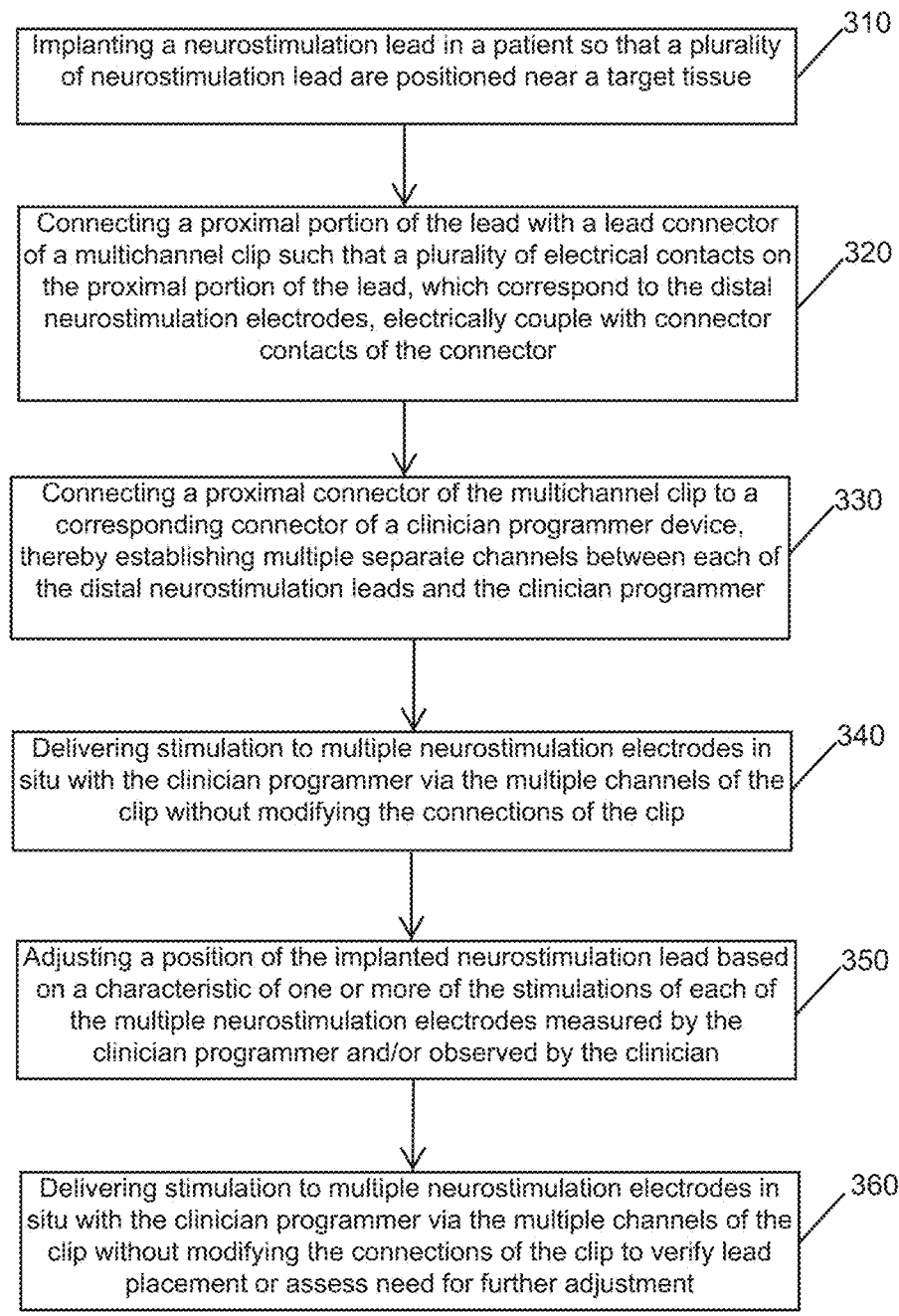

FIGS. 14-16 illustrate example methods of using a multichannel clip in accordance with embodiments of the invention. As described in FIG. 14, the methods herein can apply to coupling electrical components of various differing types of devices to a single test device to allow rapid testing of multiple components without requiring a user to separately attach electrical contacts for each component to a probe or test device. Such methods herein are particularly advantageous when used in testing or verifying of multiple neurostimulation electrodes of an implanted neurostimulation lead that is performed in situ with a clinician programmer, as described in the method of FIG. 14, in particular during a lead placement procedure, as detailed in the method of FIG. 16.

FIG. 14 depicts a method of testing, verifying or programming a first device having multiple electrical components. The method includes steps of: Electrically connecting a distal connector of a multichannel clip with a portion of a first device having multiple electrical contacts corresponding to multiple electrical components of the device 110, Electrically connecting a proximal connector of the multichannel clip with a corresponding connector of a second device configured for testing and/or programming 120 and Performing a testing, verification or programming procedure of the multiple electrical components with the second device by delivering stimulation individually to the multiple electrical components via multiple separate channels provided by the multichannel clip electrically coupling the first and second devices 130.

FIG. 15 depicts a method of testing, verifying or programming multiple neurostimulation electrodes of an implanted lead in situ with a clinician programmer device via a multichannel test clip in accordance with various embodiments. The method includes steps of: Electrically connecting a lead connector of a multichannel clip with a proximal portion of an implantable neurostimulation lead having multiple electrical contacts corresponding to multiple neurostimulation electrodes on a distal portion of the lead 210, Electrically connecting a proximal connector of the multichannel clip with a corresponding connector of a testing or programming device 220, and Performing a testing, verification or programming procedure of the implanted neurostimulation lead in situ by delivering stimulation individually to multiple neurostimulation electrodes of the lead via multiple separate channel provided by the multichannel clip coupled to each of the lead and the device 230.

FIG. 16 depicts a method of placing a neurostimulation lead in a patient with a clinician programmer electrically coupled with the lead via a multichannel clip in accordance with various embodiments. The method includes steps of: Implanting a neurostimulation lead in a patient so that a plurality of neurostimulation lead are positioned near a target tissue 310, Connecting a proximal portion of the lead with a lead connector of a multichannel clip such that a plurality of electrical contacts on the proximal portion of the lead, which correspond to the distal neurostimulation electrodes, electrically couple with connector contacts of the connector 320, Connecting a proximal connector of the multichannel clip to a corresponding connector of a clinician programmer device, thereby establishing multiple separate channels between each of the distal neurostimulation leads and the clinician programmer 330, Delivering stimulation to multiple neurostimulation electrodes in situ with the clinician programmer via the multiple channels of the clip without modifying the connections of the clip 340, Adjusting a position of the implanted neurostimulation lead based on a characteristic of one or more of the stimulations of each of the multiple neurostimulation electrodes measured by the clinician programmer and/or observed by the clinician 350, and Delivering stimulation to multiple neurostimulation electrodes in situ with the clinician programmer via the multiple channels of the clip without modifying the connections of the clip to verify lead placement or assess need for further adjustment 360.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A multichannel clip for testing of a plurality of electrical components of a first device with a second device, the clip comprising:
    a pair of opposing members that are pivotally coupled so as to be movable between an open position and closed position such that, in the open position, the opposing members are spaced apart to receive a contact portion of the first device therebetween, the contact portion having contacts electrically coupled with the plurality of electrical components and, in the closed position, the opposing members are positioned adjacent each other to secure the contact portion of the first device therebetween;
    a plurality of electrical contacts positioned on an inside surface between the opposing members so as to electrically couple with the plurality of electrical contacts on the contact portion of the first device secured between the opposing members in the closed position;
    a proximal cable connector, the proximal cable connector having a plurality of connector contacts and configured for electrically coupling with the second device; and
    a stimulation cable having a plurality of conductors extending therethrough electrically coupling the plurality of electrical contacts of the clip to the proximal cable connector, wherein the plurality of conductors correspond to the plurality of electrical contacts of the clip such that each of the conductors provides a separate channel between a respective electrical component of the plurality of electrical components and the second device so as to allow testing of each of the plurality of electrical components of the first device with the second device via the clip,
    wherein the multi-channel clip is configured such that each channel allows stimulating and measuring with the second device concurrently, in a rapid sequence, or in varying combinations.

2. The multichannel clip of claim 1, wherein the stimulation cable and associated proximal cable connector are permanently and fixedly attached to the test-clip.

3. The multichannel clip of claim 1, wherein the plurality of connector contacts comprise a plurality of pins.

4. The multichannel clip of claim 3, wherein the proximal cable connector and the plurality of pins disposed within are configured in accordance with a connector standard compatible for connection with the second device.

5. The multichannel clip of claim 1, wherein the proximal connector is configured according to a connector standard.

6. The multichannel clip of claim 1, wherein the opposing members define a pair of jaws that are biased toward the closed position by one or more springs.

7. The multichannel clip of claim 1, wherein each of the pair of opposing members includes a handle, wherein at least one handle of the pair of opposing members includes a gripping surface to facilitate manual actuation of the clip with a single hand of a user.

8. The multichannel clip of claim 1 further comprising:
    a connector holder disposed between the pair of opposing members.

9. The multichannel clip of claim 8, wherein the connector holder includes top and bottom portions that are pivotally coupled such that the top and bottom portions engage the portion of the first device when the opposing members are in the closed position.

10. The multichannel clip of claim 9, wherein the connector holder is molded to correspond to a shape of the contact portion of the first device being secured within the clip.

11. The multichannel clip of claim 10, wherein the connector holder is molded asymmetrically so as to only receive the portion of the first device in a pre-determined orientation.

12. The multichannel clip of claim 10, further including:
    a graphical representation viewable by a user that indicates a desired position and/or orientation of the portion of the contact portion of the first device within the clip to assist a user in placement of the portion of the first device within the clip.

13. The multichannel clip of claim 1, wherein the first device is a neurostimulation device and the electrical components are neurostimulation electrodes of the neurostimulation device.

14. The multichannel clip of claim 8, wherein the plurality of electrical contacts of the clip are defined by a plurality of electrical pins mounted on a printed circuit board disposed within one of the pair of opposing members.

15. The multichannel clip of claim 14, wherein the connector holder includes a plurality of openings through which the plurality of electrical pins extend so as to engage the plurality of electrical contacts on the contact portion of the first device when secured between the pair of opposing members in the closed position.

16. The multichannel clip of claim 1, wherein the plurality of electrical contacts of the clip are positioned in an arrangement that corresponds to that of the electrical contacts on the contact portion of the first device.

17. A multichannel clip for use in testing of a plurality of electrodes in a first device with a programming device, the clip comprising:
- a pair of jaws pivotally coupled and movable between an open position in which a distal portion of each of the jaws are spaced apart and a closed position in which the jaws secure a contact portion of the first device therebetween, the portion having a plurality of electrical contacts corresponding to a plurality of electrodes of the first device;
- a plurality of electrical contacts positioned within the clip so as to electrically couple with the plurality of electrical contacts on the contact portion of the first device when secured between the pair of jaws in the closed position;
- a manually operable actuator for facilitating movement of the pair of jaws between the closed position and the open position to facilitate removal of the contact portion of the first device from the closed position; and
- a stimulation cable having a plurality of conductors extending therethrough electrically coupling the plurality of electrical contacts to a proximal cable connector, wherein the proximal cable connector includes a plurality of connector contacts and is configured for connection with the programming device, wherein the plurality of conductors correspond to the plurality of electrical contacts of the clip such that each of conductors provides a separate channel between the plurality of electrodes of the first device and the programming device,
- wherein the clip is configured to allow stimulating and measuring with the programming device through each separate channel concurrently, in a rapid sequence or in varying combinations.

18. The multichannel clip of claim 17, wherein the plurality of electrical contacts of the clip are concurrently electrically coupled with the plurality of electrical contacts of the first device portion when secured in the closed position and wherein the stimulation cable and proximal cable end connector are permanently and fixedly attached to the test-clip such that a user can stimulate the plurality of electrodes concurrently or in a rapid sequence with the programming device without adjusting any electrical connections of the clip between stimulations.

19. A multichannel clip for use in testing of a plurality of electrical components of a first device with a second device, the clip comprising:
- a clip having a first portion and a second portion movable relative each other between an open position in which the top and bottom portions are spaced apart and a closed position in which the top and bottom portions are urged towards each other, the open position being suitable for receiving a contact portion of the first device, the portion having a plurality of electrical contacts corresponding to a plurality of electrical components of the first device, and the closed position being suitable for securing the contact portion of the first device between the first and second portions;
- a plurality of electrical contacts positioned so as to electrically couple with the plurality of electrical contacts on the contact portion of the first device when secured between the first and second portions in the closed position; and
- a stimulation cable having a plurality of conductors extending therethrough electrically coupling the plurality of electrical contacts to a proximal cable connector, wherein the proximal cable connector includes a plurality of connector contacts and is configured for electrically coupling with the second device so as to allow verification and/or testing of each of the plurality of electrical components of the first device with the second device when coupled to the connector,
- wherein the clip is configured to allow stimulating and measuring with the second device through each separate channel concurrently, in a rapid sequence or in varying combinations.

20. The multichannel clip of claim 19, further comprising:
- a manually operable actuation mechanism that effects movement of the first and second portions of the clip relative each other when in the closed position so as to facilitate release of the contact portion of the first device from the clip.

21. A method of verifying and/or testing a plurality of electrical components of a first device with a second device, the method comprising:
- providing a multichannel clip having opposing members movable between an open position and a closed position;
- securing a contact portion of a first device between opposing members of the clip in the closed position, wherein the clip includes a plurality of connector contacts disposed along an inside surface between the opposing members so as to electrically couple with a plurality of electrical contacts of the first device that correspond to the plurality of electrical components;
- connecting a proximal cable connector of the clip to a corresponding connector of the second device, wherein the proximal cable connector is a multichannel connector having a plurality of connector contacts that correspond to and are electrically coupled with the plurality of connector contacts disposed between the opposing members via a plurality of electrical conductors such that the clip provides a separate channel between each of the plurality of electrical components of the first device and the second device; and
- verifying and/or testing each of the plurality of electrical components of the first device with the second device via the multichannel clip closed on the contact portion of the first device remains secured between opposing members and connected to the second device, wherein verifying and/or testing of each of the plurality of electrical components is performed through each separate channel of the multi-channel clip concurrently, in a rapid sequence or in varying combinations.

22. The method of claim 21, wherein the second device comprises a programming device.

23. The method of claim 22, wherein the first device comprises a neurostimulation device.

24. The method of claim 21, wherein verifying and/or testing each of the plurality of electrical components comprises communicating, stimulating and/or measuring through the separate channels provided by the multichannel clip.

25. The method of claim 24, wherein the communicating, stimulating and/or measuring through the separate channels occurs concurrently.

26. The method of claim 21, wherein verifying and/or testing each of the plurality of electrical components comprises multi-plexing through the separate channels with the second device.

27. The method of claim 21, wherein multi-plexing through the separate channels with the second device utilizes a pre-determined programmable instruction stored on a readable memory accessed by the second device.

28. The method of claim 21, wherein verifying and/or testing comprises communicating with a third device communicatively coupled with the multichannel clip.

29. The method of claim 28, wherein the second device comprises a power source and/or measuring device and the third device comprises a control device and/or programming device.

30. The method of claim 21, further comprising:
  manually actuating an actuation mechanism of the clip to effect removal of the portion of the first device from the opposing members of the clip.

31. The method of claim 21, wherein verification and/or testing of each of the plurality of electrical components of the first device is carried out without re-positioning or re-adjusting the multichannel clip.

32. The multi-channel clip of claim 1, wherein the multi-channel clip is configured to electrically couple the first device without any intervening connection cables.

33. The method of claim 21, wherein the multi-channel clip electrically couples the first device to the second device without any intervening connection cables.

* * * * *